US008343719B2

(12) United States Patent
Ju et al.

(10) Patent No.: US 8,343,719 B2
(45) Date of Patent: Jan. 1, 2013

(54) MICRORNA AS BIOMARKER IN CANCER

(75) Inventors: Jingfang Ju, Mobile, AL (US); Yaguang Xi, Mobile, AL (US); Nakajima Go, Tokyo (JP)

(73) Assignee: Research Foundation of State University of New York, Albany, NY (US)

( * ) Notice: Subject to any disclaimer, the term of this patent is extended or adjusted under 35 U.S.C. 154(b) by 0 days.

(21) Appl. No.: 12/513,007

(22) PCT Filed: Oct. 30, 2007

(86) PCT No.: PCT/US2007/083005
§ 371 (c)(1),
(2), (4) Date: Mar. 31, 2010

(87) PCT Pub. No.: WO2008/055158
PCT Pub. Date: May 8, 2008

(65) Prior Publication Data
US 2010/0203513 A1    Aug. 12, 2010

Related U.S. Application Data

(60) Provisional application No. 60/855,233, filed on Oct. 30, 2006.

(51) Int. Cl.
*C12Q 1/68* (2006.01)
(52) U.S. Cl. ............ 435/6; 435/325; 435/375; 536/24.5
(58) Field of Classification Search ........................ None
See application file for complete search history.

(56) References Cited

U.S. PATENT DOCUMENTS

| | | | |
|---|---|---|---|
| 2005/0059005 A1* | 3/2005 | Tuschl et al. .................. | 435/6 |
| 2005/0182005 A1* | 8/2005 | Tuschl et al. .................. | 514/44 |
| 2005/0266418 A1 | 12/2005 | Chen et al. | |

FOREIGN PATENT DOCUMENTS
WO    WO 2005/078139 A2 *    8/2005

OTHER PUBLICATIONS

Lilja et al. (2008) "Prostate-specific antigen and prostate cancer: prediction, detection and monitoring" Nat Rev Cancer. Apr. 2008;8(4):268-78.*
Tricoli et al. (2007) "MicroRNA: Potential for Cancer Detection, Diagnosis, and Prognosis" Cancer Res 2007; 67 (10): 4553-4555.*
McManus 2003, Seminars in Cancer Biology 13:253-258.*
Calin et al. 2002, PNAS 99:15524-15529.*
Volinia et al. PNAS Feb. 2006, vol. 103, No. 7:2257-2261.*
Xi et al., "Prognostic Values of nicroRNAs in Colorectal Cancer", Biomarker Insights, (2006), vol. 1, pp. 113-121.
Calin et al., "MicroRNA-Cancer Connection: The Beginning of a New Tale", Cancer Res., (Aug. 1, 2006), vol. 66, No. 15, pp. 7390-7394.
Nakajima et al., "Non-coding MicroRNAs hsa-let-7g and hsa-miR-181b are Associated with Chemoresponse to S-1 in Colon Cancer",
Cancer Genomics Proteomics, (Oct. 3, 2006), vol. 3, No. 5; pp. 317-324.
Calin et al., "A MicroRNA Signature Associated with Prognosis and Progression in Chronic Lymphocytic Leukemia", The New England Journal of Medicine, (Oct. 27, 2005), vol. 353, No. 17, pp. 1793-1801.
Schratt et al., "A brain-specific microRNA regulates dendritic spine development", Nature Publishing Group, (Jan. 19, 2006), vol. 439, No. 19, pp. 283-289.
Lau et al., "An Abundant Class of Tiny RNAs with Probable Regulatory Roles in Caenorhabditis elegans", Science, (Oct. 26, 2001), vol. 294, pp. 858-862.
Lee et al., "An Extensive Class of Small RNAs in Caenorhabditis elegans", Science, (Oct. 26, 2001), vol. 294, pp. 862-864.
Brennecke et al., "Bantam Encodes a Developmentally Regulated microRNA that Controls Cell Proliferation and Regulates the Proapoptotic Gene hid in Drosophila", Cell, (Apr. 4, 2003), vol. 113, pp. 25-36.
Arango et al., "c-myc/p53 Interaction Determines Sensitivity of Human Colon Carcinoma Cells to 5-Fluorouracil in Vitro and in Vivo", Cancer Research, (Jun. 15, 2001), vol. 61, pp. 4910-4915.
Salonga et al., "Colorectal Tumors Responding to 5-Fluorouracil Have Low Gene Expression Levels of Dihydropyrimidine Dehydrogenase, Thymidylate Synthase, and Thymidine Phosphorylase", Clinical Cancer Research, (Apr. 2000), vol. 6, pp. 1322-1327.
Akervall et al., "Cyclin D1 Overexpression versus Response to Induction Chemotherapy in Squamous Cell Carcinoma of the Head and Neck", Acta Oncologica, (2001), vol. 40, No. 4, pp. 505-511.
Xi et al., "Differentially Regulated Micro-RNAs and Actively Translated Messenger RNA Transcripts by Tumor Suppressor p53 in Colon Cancer", Clin. Cancer Res., (Apr. 1, 2006), vol. 12, No. 7, pp. 2014-2024.
Elliott et al., "E2F-1 Gene Therapy Induces Apoptosis and Increases Chemosensitivity in Human Pancreatic Carcinoma Cells", Tumor Biology, (2002), vol. 23, pp. 76-86.
Van Den Brande et al., "EORTC Early Clinical Studies Group early phase II trial of S-I in patients with advanced or metastatic colorectal cancer", British Journal of Cancer, (2003), vol. 88, pp. 648-653.
Heidelberger et al., "Fluorinated Pyrimidines, A New Class of Tumour-Inhibitory Compounds", Nature, (Mar. 30, 1957), No. 4561, pp. 663-666.
Lagos-Quintana et al., "Identification of Novel Genes Coding for Small Expressed RNAs", Science, (Oct. 26, 2001), vol. 294, pp. 853-858.
Lagos-Quintana et al., "Identification of Tissue-Specific MicroRNAs from Mouse", Current Biology, (Apr. 30, 2002), vol. 12, pp. 735-739.

(Continued)

*Primary Examiner* — Kimberly Chong
(74) *Attorney, Agent, or Firm* — The Webb Law Firm

(57) ABSTRACT

The present invention relates to the discovery of certain microRNAs that correlate with certain information regarding cancer. The microRNAs of the invention are selected from the group consisting of hsa-miR-15b, hsa-miR-181b, hsa-miR-191, hsa-miR-200c, and hsa-let-7g. If the expression of these microRNAs is increase, then the increased expression of these microRNAs is diagnostic for cancer, characterizes the cancer, prognosticates an expected response to cancer treatments, and/or prognosticates an expected survival of a patient. Embodiments of this discovery include a method, composition, kit and isolated nucleic acid.

13 Claims, 17 Drawing Sheets

OTHER PUBLICATIONS

Reinhart et al., "MicroRNAs in plants", Genes & Development, (2002), vol. 16, pp. 1616-1626.

Mourelatos et al., "miRNPs: a noval class of ribonucleoproteins containing numerous microRNAs", Genes & Development, (2002), vol. 16, pp. 720-728.

Lagos-Quintana et al., "New microRNAs from mouse and human", RNA, (2003), vol. 9, pp. 175-179.

Banerjee et al., "Novel aspects of resistance to drugs targeted to dihydrofolate reductase and thymidylate synthase", Biochimica et Biophysica Acta, (2002), vol. 1587, pp. 164-173.

McDermott et al., "Molecular and biochemical markers in colorectal cancer", European Society for Medical Oncology, (2002), 13 Suppl. 4, pp. 235-245.

Vallbohmer et al., "Molecular factors of 5-fluorouracil metabolism in colorectal cancer: Analysis of primary tumor and lymph node metastasis", International Journal of Oncology, (2006), vol. 28, pp. 527-533.

Ajani et al., "Multicenter Phase II Trial of S-1 Plus Cisplatin in Patients With Untreated Advanced Gastric or Gastroesophageal Junction Adenocarcinoma", Journal of Clinical Oncology, (Feb. 1, 2006), vol. 24, No. 4, pp. 663-667.

Klampfer et al., "Oncogenic Ras increases sensitivity of colon cancer cells to 5-FU-induced apoptosis", Oncogene (2005), vol. 24, pp. 3932-3941.

Klampfer et al., "Oncogenic Ras Promotes Butyrate-induced Apoptosis through Inhibition of Gelsolin Expression", The Journal of Biological Chemistry, (Aug. 27, 2004), vol. 279, No. 35, pp. 36680-36688.

Elsaleh et al., "p53 Gene Mutation, Microsatellite Instability and Adjuvant Chemotherapy: Impact on Survival of 388 Patients with Dukes' C Colon Carcinoma", Oncology, (2000), vol. 58, pp. 52-59.

Shirao et al., "Phase II Study of Oral S-1 for Treatment of Metastatic Colorectal Carcinoma", Cancer, (Jun. 1, 2004), vol. 100, No. 11, pp. 2533-2361.

Ohtsu et al., "Phase II study of S-1, a novel oral fluoropyrimidine derivative, in patients with metastatic colorectal carcinoma", British Journal of Cancer (2000), vol., 83, No. 2, pp. 141-145.

Johnson et al., "RAS Is Regulated by the let-7 MicroRNA Family", Cell, (Mar. 11, 2005), vol. 120, pp. 635-647.

Michael et al., "Reduced Accumulation of Specific MicroRNAs in Colorectal Neoplasis", Molecular Cancer Research, (Oct. 2003), vol. 1, pp. 882-891.

Reinhart et al., "The 21-nucleotide let-7 RNA regulates development timing in Caenorhabditis elegans", Nature, (Feb. 24, 2000), vol. 403, pp. 901-906.

Lee et al., "The C. elegans Heterochronic Gene lin-4 Enclodes Small RNAs with Antisense Complementarity to lin-14", Cell, (Dec. 3, 1993), vol. 75, pp. 843-854.

Xu et al., "The Drosophila MicroRNA Mir-14 Suppresses Cell Death and Is Required for Normal Fat Metabolism", Current Biology, (Apr. 29, 2003), vol. 13, pp. 790-795.

Schoffski, "The modulated oral fluoropyrimidine prodrug S-1, and its use in gastrointestinal cancer and other solid tumors", Anti-Cancer Drugs, (2004), vol. 15, No. 2, pp. 85-106.

Chen et al., "The role of microRNA-1 and microRNA-133 in skeletal muscle proliferation and differentiation", Nat. Genet., (Feb. 2006), vol. 38, No. 2, pp. 228-233.

Wang et al., "Analyses of p53 Target Genes in the Human Genome by Bioinformatic and Microarray Approaches", The Journal of Biological Chemistry, (Nov. 23, 2001), vol. 276, No. 47, pp. 43604-43610.

Krek et al., "Combinatorial microRNA target predictions", Nature Genetics, (May 2005), vol. 37, No. 5, pp. 495-500.

Xi et al., "Differentially Regulated Micro-RNAs and Actively Translated Messenger RNA Transcripts by Tumor Suppressor p53 in Colon Cancer", Clin. Cancer Res. (Apr. 1, 2006), vol. 12, No. 7, pp. 2014-2024.

Bunz et al., "Disruption of p53 in human cancer cells alters the responses to therapeutic agents", The Journal of Clinical Investigation, (Aug. 1999), vol. 104, No. 3, pp. 263-269.

Yu et al., "Effect of p53 Status on Tumor Response to Antiangiogenic Therapy", Science (2002), vol. 295, pp. 1526-1528.

Calin et al., "Frequent deletions and down-regulation of micro-RNA genes miR15 and miR16 at 13q14 in chronic lymphocytic leukemia", PNAS, (Nov. 26, 2002), vol. 99, No. 24, pp. 15524-15529.

John et al., Human MicroRNA Targets, PLoS Biology, (Nov. 2004), vol. 2, Issue 11, pp. 1862-1879.

Bandres, et al., "Identification by Real-time PCT of 13 mature microRNAs differentially expressed in colorectal cancer and non-tumoral tissues", Molecular Cancer, (2006), vol. 5, No. 29, pp. 1476-4598.

Belvedere et al., "Lack of correlation between immunohistochemical expression of E2F-1, thymidylate synthase expression and clinical response to 5-fluorouracil in advanced colorectal cancer", Annals of Oncology, (2004), vol. 15, pp. 55-58.

Benard et al., "Micro-ARN et oncogenese", Bull Cancer, (2005), vol. 92, No. 9, pp. 757-762.

Wienholds et al., "MicroRNA function in animal development", FEBS Letters, (2005), vol. 579, pp. 5911-5922.

Chen et al., "microRNA-guided posttranscriptional gene regulation", Biol. Chem., (Dec. 2005), vol. 386, pp. 1205-1218.

Hammond, "MicroRNAs as oncogenes", Genetics & Development, (2006), vol. 16, pp. 4-9.

Hampton, "MicroRNAs Move Into Cancer Research", JAMA, (Jul. 27, 2005), vol. 294, No. 4, pp. 411-412.

Calin et al., "MicroRNA profiling reveals distinct signatures in B cell chronic lymphocytic leukemias", PNAS, (Aug. 10, 2004), vol. 101, No. 32, pp. 11755-11760.

Bartel, "MicroRNAs: Genomics, Biogenesis, Mechanism, and Function", Cell, (Jan. 23, 2004), vol. 116, pp. 281-297.

Cimmino et al., "miR-15 and miR-16 induce apoptosis by targeting BCL2", PNAS, (Sep. 27, 2005), vol. 102, No. 39, pp. 13944-13949.

Bottoni et al., "miR-15a and miR-16-1 Down-Regulation in Pituitary Adenomas", Journal of Cellular Physiology, (2005), vol. 204, pp. 280-285.

Mosner et al., "Negative feedback regulation of wild-type p53 biosynthesis", The EMBO Journal, (1995), vol. 14, No. 18, pp. 4442-4449.

Esquela-Kerscher et al., "Oncomirs—microRNAs with a role in cancer", Nature Reviews-Cancer, (Apr. 2006), vol. 6, pp. 259-269.

Ju et al., "Regulation of p53 expression by thymidylate synthase", Cell Biology, (Mar. 1999), vol. 96, pp. 2769-3774.

Sinha et al., "Relationships between proto-oncogene expression and apoptosis induced by anticancer drugs in human prostate tumor cells", Biochimica et Biophysica Acta, (1995), vol. 1270, pp. 12-18.

Draghici et al., "Reliability and reproducibility issues in DNA microarray measurements", Trends Genet., (Feb. 2006), vol. 22, No. 2, pp. 101-109.

Bunz et al., "Requirement for p53 and p21 to Sustain G2 Arrest After DNA Damage", Science, (Nov. 20,1998), vol. 282, pp. 1497-1501.

Ju et al., "Simultaneous gene expression analysis of steady-state and actively translated mRNA populations from osteosarcoma MG-63 cells in response to IL-1a via an open expression analysis platform", Nucleic Acids Research, (2003), vol. 31, No. 17, pp. 5157-5166.

Mattick et al., "Small regulatory RNAs in mammals", Human Molecular Genetics, (2005), vol. 14, Review Issue 1, pp. R121-R132.

Lee, et al., "The C. elegans Heterochronic Gene lin-4 Encodes Small RNAs with Antisense Complementarity to lin-14", Cell, (Dec. 3, 1993), vol. 75, pp. 843-854.

Cummins et al., "The colorectal microRNAome", PNAS, (Mar. 7, 2006), vol. 103, No. 10, pp. 3687-3692.

Fu et al., "Translational regulation of human p53 gene expression", The EMBO Journal, (1996), vol. 15, No. 16, pp. 4392-4401.

Chu et al., "Thymidylate Synthase Protein and p53 mRNA Form an in Vivo Ribonucleoprotein Complex", Molecular and Cellular Biology, (Feb. 1999), vol. 19, No. 2, pp. 1582-1594.

Chu et al., "Identification of a Thymidylate Synthase Ribonucleoprotein Complex in Human Colon Cancer Cells", Molecular and Cellular Biology, (Jan. 1994), vol. 14, No. 1, pp. 207-213.

* cited by examiner

FIG. 1

| Characteristics | Frequency | Percentage (%) |
|---|---|---|
| Age(Years) | | |
| Mean(range) | 62(30-93) | |
| Gender | | |
| Male | 14 | 58.3 |
| Female | 10 | 41.7 |
| Anatomic site | | |
| Ascending colon | 3 | 12.5 |
| Transverse colon | 2 | 8.3 |
| Descending colon | 4 | 16.7 |
| Sigmoid colon | 3 | 12.5 |
| Rectum | 12 | 50.0 |
| Histology | | |
| Adenocarcinoma | 24 | 100 |
| UICC stage | | |
| I | 4 | 16.7 |
| II | 4 | 16.7 |
| III | 8 | 33.3 |
| IV | 8 | 33.3 |
| Survival (Months) | | |
| Mean(range) | 30(0-75) | |
| 0-20 | 3 | 12.5 |
| 20-50 | 20 | 83.3 |
| >50 | 1 | 4.2 | miR-181b

CR = complete response
PR = partial response
NC = no change
PD = progressive disease.

CR = complete response

PR = partial response

NC = no change

PD = progressive disease.

MICRORNA AS BIOMARKER IN CANCER

SUMMARY OF THE INVENTION

The present invention relates to the discovery that certain microRNAs can be used to detect or diagnose and prognosticate a cancer. These microRNAs can be used in a method of detecting or diagnosing a precancerous lesion or cancer, prognosticating an expected response to a cancer treatment, or prognosticating an expected survival of a subject with cancer; a composition used to diagnose a cancer or prognosticate a cancer; a kit for diagnosing or prognosticating a cancer, or an isolated nucleic acid.

One aspect of the method of detecting or diagnosing a cancer, prognosticating an expected response of a subject to a cancer treatment, or prognosticating an expected survival of a subject comprises the following steps. A biological sample is obtained from a subject in need of diagnosis, or response or survival prognostication. The amount of a microRNA in the biological sample is measured. The microRNA that is measured is selected from the group consisting of hsa-miR-15b, hsa-miR-181b, hsa-miR-191, hsa-miR-200c, and hsa-let-7g. The measured amount of microRNA is compared to a standard amount of microRNA found in a normal or non-cancerous cell, or to an amount of microRNA in a control sample. An increased level, amplification or over-expression of microRNA relative to the standard or the control is diagnostic for cancer, is prognostic for a low expected response to the cancer treatment, or is prognostic for a low expected survival, of the subject. Alternatively, if a normal level of the microRNA relative to the standard or the control is measured, then the normal level is diagnostic for the absence of cancer, prognostic for a high expected response to a cancer treatment, or prognostic for a high expected survival, of the subject.

Another aspect of the method of detecting or diagnosing a cancer, prognosticating an expected response by a subject to a cancer treatment, or prognosticating an expected survival of a subject comprises the following steps. A biological sample containing RNA from a subject in need of diagnosis, or response or survival prognostication is obtained. The biological sample is reacted with a reagent capable of binding to a microRNA selected from the group consisting of hsa-miR-15b, hsa-miR-181b, hsa-miR-191, hsa-miR-200c, and hsa-let-7g. The reaction forms a measurable microRNA. The amount of measurable microRNA present in the sample is then measured, and compared to a standard amount of the microRNA found in a normal cell or non-cancerous cell, or to an amount of the microRNA found in a control sample. An increased level or over-expression of microRNA in the sample relative to the standard or control indicates at least one of the following: the sample contains a cancer cell or precancerous cell; the expected response by the subject to a cancer treatment is low; or the expected survival of the subject is low. Likewise, a normal level or normal expression of the microRNA in the sample relative to the standard or control indicate: the sample does not contain a cancer cell or precancerous cell; the expected response by the subject to the cancer treatment is high, or the expected survival of the subject with cancer is high.

These microRNAs also relate to a composition to diagnose or prognosticate a cancer. In one aspect, the composition comprises a compound capable of binding to at least a portion of a microRNA selected from the group consisting of hsa-miR-15b, hsa-miR-181b, hsa-miR-191, hsa-miR-200c, and hsa-let-7g. If the compound is bound to at least a portion of the microRNA, it folios a measurable complex. A sample having an amplified amount of the measurable complex is diagnostic for the cancer, is prognostic for a low expected response to the cancer treatment, or is prognostic for a low expected survival, of the subject. Likewise, a sample having a normal amount of the measurable complex is diagnostic for the absence cancer, is prognostic for a high expected response to the cancer treatment, or is prognostic for a high expected survival, by the subject.

These microRNAs also relate to a kit for diagnosing or prognosticating a cancer. In one aspect, the kit comprises a composition capable of binding to at least a portion of a microRNA over-expressed by a cancer cell. The microRNA is selected from the group consisting of hsa-miR-15b, hsa-miR-181b, hsa-miR-191, hsa-miR-200c, and hsa-let-7g. If it is determined that the microRNA is over-expressed in the sample, the over-expression of the microRNA is diagnostic for the cancer, or indicates a poor prognosis for the subject's expected response to a cancer treatment, or indicates a poor prognosis for the expected survival of the subject with cancer. If it is determined that the microRNA is at normal levels in the sample, the normal levels of the microRNA is diagnostic for the absence of cancer, indicates a good prognosis for the subject's expected response to a cancer treatment, or indicates a good prognosis for expected survival of the subject with cancer.

These microRNAs also relate to an isolated nucleic acid. In one aspect, the isolated nucleic acid comprises at least two nucleic acids. The first nucleic acid molecule is capable of hybridizing to at least a portion of a first target nucleic acid molecule selected from the group consisting of hsa-miR-15b, hsa-miR-181b, hsa-miR-191, hsa-miR-200c, and hsa-let-7g. The first nucleic acid further comprises at least 10 nucleotides being at least 90% complementary to the first target nucleic acid molecule. The second nucleic acid molecule is capable of hybridizing to at least a portion of a second target. The second target is selected from the group consisting of hsa-miR-15b, hsa-miR-181b, hsa-miR-191, hsa-miR-200c, and hsa-let-7g, but is different from the first target. The second nucleic acid further comprises at least 10 nucleotides being at least 90% complementary to the second target nucleic acid molecule.

Other applications and advantages afforded by the present invention will be apparent from the detailed description and exemplification hereinbelow.

BRIEF DESCRIPTION OF THE DRAWING(S)

FIG. 1 is a table of the clinical features of the 24 patients studied in Experiment 1.

DETAILED DESCRIPTION OF THE INVENTION

Figure 2:
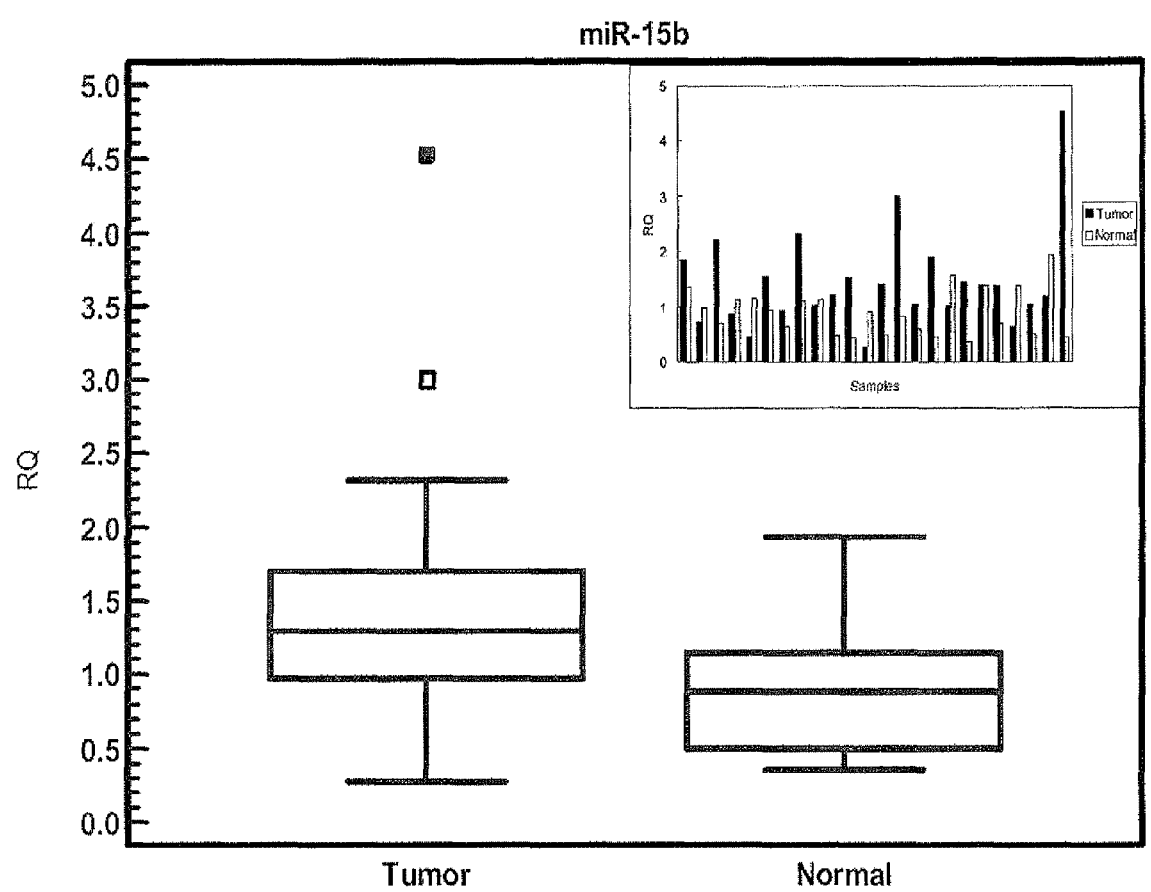
FIG. 2 is a graph depicting the levels of hsa-miR-15b in cancer cells and normal cells obtained from the patients studied in Experiment 1. The small chart contained within the graph displays the microRNA expression for all individual paired samples.

The term "binding", "to bind", "binds", "bound" or any derivation thereof refers to any stable, rather than transient, chemical bond between two or more molecules, including, but not limited to, covalent bonding, ionic bonding, and hydrogen bonding. Thus, this term also encompasses hybridization between two nucleic acid molecules among other types of chemical bonding between two or more molecules.

It is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only the appended claims.

DESCRIPTION OF THE INVENTION

One aspect of the invention is a method of detecting or diagnosing cancer, prognosticating an expected response to a cancer treatment, or prognosticating an expected survival. First, a biological sample from a subject in need of diagnosis, or response or survival prognostication is obtained. Second, an amount of a microRNA selected from the group consisting of hsa-miR-15b, hsa-miR-181b, hsa-miR-191, hsa-miR-200c, and hsa-let-7g is measured from the biological sample. Third, the amount of microRNA detected in the sample is compared to either a standard amount of microRNA present in a normal cell or a non-cancerous cell, or an amount of the microRNA present in the control sample. If the amount of microRNA in the sample is greater than the amount of microRNA in the standard or control sample, then the subject is diagnosed as having cancer, the prognosis is a low expected response to the cancer treatment, or the prognosis is a low expected survival of the subject. The prognoses are relative to a subject with cancer having normal levels of the microRNA, or relative to the average expected response or survival of a patient having the cancer.

Another embodiment of the method of detecting or diagnosing cancer, prognosticating an expected response to a cancer treatment, or prognosticating an expected survival comprises the following steps. First, a biological sample containing RNA is obtained from the subject. The biological sample is reacted with a reagent capable of binding to a microRNA selected from the group consisting of hsa-miR-15b, hsa-miR-181b, hsa-miR-191, hsa-miR-200c, and hsa-let-7g. The reaction between the reagent and the microRNA forms a measurable microRNA. The measurable microRNA is measured, and then compared to either the standard or the control.

The invention can be practiced on any multi-cellular eukaryotic subject that has any risk of developing cancer. Particularly, the invention is most useful when practiced on a mammalian subject, and most useful when practiced on humans.

Samples to be used in the invention can be obtained in any manner known to a skilled artisan. The sample optimally should only include tissue believed to be cancerous, such as a portion of a surgically removed tumor. However, the invention is not limited to just tissue believed to be cancerous. Instead, samples can be derived from any part of the subject containing at least some tissue believed to be cancerous.

Measuring the amount of microRNA can be performed in any manner known by one skilled in the art of measuring the quantity of RNA within a sample. An example of a method for quantifying microRNA is quantitative reverse transcriptase polymerase chain reaction. Another example of a method of quantifying microRNA is as follows: hybridizing at least a portion of the microRNA with a fluorescent nucleic acid, and reacting the hybridized microRNA with a fluorescent reagent, wherein the hybridized microRNA emits a fluorescent light. Another method of quantifying the amount of microRNA in a sample is by hybridizing at least a portion the microRNA to a radio-labeled complementary nucleic acid. In instances when a nucleic acid capable of hybridizing to the microRNA is used in the measuring step, the nucleic acid is at least 5 nucleotides, at least 10 nucleotides, at least 15 nucleotides, at least 20 nucleotides, at least 25 nucleotides, at least 30 nucleotides or at least 40 nucleotides; and may be no longer than 25 nucleotides, no longer than 35 nucleotides; no longer than 50 nucleotides; no longer than 75 nucleotides, no longer than 100 nucleotides or no longer than 125 nucleotides in length. The nucleic acid is any nucleic acid having at least 80% homology, 85% homology, 90% homology, 95% homology or 100% homology with any of the complementary sequences for the microRNAs selected from the group consisting of hsa-miR-15b, hsa-miR-181b, hsa-miR-191, hsa-miR-200c, and hsa-let-7g.

The amount of microRNA is compared to either a standard amount of the microRNA present in a normal cell or a non-cancerous cell, or to the amount of microRNA in a control sample. The comparison can be done by any method known to a skilled artisan. An example of comparing the amount of the microRNA in a sample to a standard amount is comparing the ratio between 5S rRNA and the microRNA in a sample to a published or known ratio between 5S rRNA and the microRNA in a normal cell or a non-cancerous cell. An example of comparing the amount of microRNA in a sample to a control is by comparing the ratios between 5S rRNA and the microRNA found in the sample and in the control sample.

In instances when the amount of microRNA is compared to a control, the control sample may be obtained from any source known to have normal cells or non-cancerous cells. Preferably, the control sample is tissue from the subject believed to contain only normal cells or non-cancerous cells.

Another aspect of the invention is a composition for detecting or diagnosing a cancer, or prognosticating an expected response or an expected survival of a subject having cancer. The inventive composition can be used in the inventive method (embodiments of which are described above). The composition comprises a compound capable of binding to at least a portion of a microRNA selected from the group consisting of hsa-miR-15b, hsa-miR-181b, hsa-miR-191, hsa-miR-200c, and hsa-let-7g. One embodiment of the inventive composition comprises a compound capable of binding to at least a portion of a microRNA selected from the group consisting of hsa-miR-181b, hsa-miR-200c, and hsa-let-7g; a compound capable of binding to hsa-miR-181b; or a compound capable of binding to hsa-miR-200c; or a compound capable of binding to hsa-let-7g. The compound capable of binding to the microRNA can be any compound known to a skilled artisan as being able to bind to the microRNA in a manner that enables one to detect the presence and the amount of the microRNA. An example of a compound capable of binding the microRNA is a nucleic acid capable of hybridizing to the microRNA. The nucleic acid has at least 5 nucleotides, at least 10 nucleotides, at least 15 nucleotides, at least 20 nucleotides, at least 25 nucleotides, at least 30 nucleotides or at least 40 nucleotides; and no longer than 25 nucleotides, no longer than 35 nucleotides; no longer than 50 nucleotides; no longer than 75 nucleotides, no longer than 100 nucleotides or no longer than 125 nucleotides in length. The nucleic acid is any nucleic acid having at least 80% homology, 85% homology, 90% homology, 95% homology or 100% homology with a sequence complementary to a microRNA selected from the group consisting of hsa-miR-15b, hsa-miR-181b, hsa-miR-191, hsa-miR-200c, and hsa-let-7g. One specific example of a nucleic acid capable of binding to the microRNA is a nucleic acid primer for use in a reverse transcriptase polymerase chain reaction.

The binding of the compound to at least a portion of the microRNA forms a measurable complex. The measurable complex is measured according to methods known to a skilled artisan. Examples of such methods include the methods used to measure the amount of the microRNA employed in the inventive method discussed above.

If there is an increased level of measurable complex relative to a standard amount of microRNA found in a normal or a non-cancerous cell, or in a control sample, then the sample either contains a pre-cancerous cell or cancer cell, thereby being diagnostic of a cancer; prognosticates an expected response to a cancer treatment; or prognosticates an expected survival of the subject.

Another embodiment of the inventive composition is a composition comprising a second compound capable of binding to a microRNA that is different from the microRNA that the first compound is capable of binding and is selected from the group consisting of hsa-miR-15b, hsa-miR-181b, hsa-miR-191, hsa-miR-200c, and hsa-let-7g. Another embodiment of the inventive composition is a composition comprising a third compound capable of binding to a microRNA that is different from the microRNA that the first and second compounds are capable of binding and is selected from the group consisting of hsa-miR-15b, hsa-miR-181b, hsa-miR-191, hsa-miR-200c, and hsa-let-7g.

Another aspect of the invention is a kit for diagnosing, or prognosticating a cancer. In one embodiment of this aspect, the kit is for diagnosing a subject with cancer. Another embodiment of this aspect is a kit for prognosticating a cancer, wherein the prognosis is an expected response by a subject to a cancer treatment. In another embodiment of this aspect, the kit is for prognosticating a cancer, wherein the prognosis is an expected survival of a subject with cancer. The kit comprises a composition capable of binding to at least a portion of a microRNA over-expressed in a cancer cell, wherein the microRNA is selected from the group consisting of hsa-miR-15b, hsa-miR-181b, hsa-miR-191, hsa-miR-200c, and hsa-let-7g, and wherein the over-expression of the microRNA is diagnostic for the cancer, or prognosticates the expected response or survival of the subject.

Another embodiment of the kit further comprising a second composition capable of binding to at least a portion of a microRNA that is different from the microRNA that can be bound by the first composition, and is selected from the group consisting of hsa-miR-15b, hsa-miR-181b, hsa-miR-191, hsa-miR-200c, and hsa-let-7g. Another embodiment of the kit is a kit further comprising a third composition capable of binding to at least a portion of a microRNA that is different from the microRNA that can be bound by the first and second compositions, and is selected from the group consisting of hsa-miR-15b, hsa-miR-181b, hsa-miR-191, hsa-miR-200c, and hsa-let-7g.

Another aspect of the invention is an isolated nucleic acid. The nucleic acid comprises a sequence being at least 80%, at least 85%, at least 90%, at least 95%, or 100% complementary to a microRNA selected from the group consisting hsa-miR-15b, hsa-miR-181b, hsa-miR-191, hsa-miR-200c, and hsa-let-7g. In another embodiment of this aspect, the isolated nucleic acid comprises a second nucleic acid that is different from the first nucleic acid and comprises a sequence being at least 80%, at least 85%, at least 90%, at least 95%, or 100% complementary to a microRNA selected from the group consisting of hsa-miR-15b, hsa-miR-181b, hsa-miR-191, hsa-miR-200c, and hsa-let-7g. In another embodiment of this aspect, the isolated nucleic acid comprises a third nucleic acid that is different from the first and second nucleic acids and comprises a sequence being at least 80%, at least 85%, at least 90%, at least 95%, or 100% complementary to a microRNA selected from the group consisting of hsa-miR-15b, hsa-miR-181b, hsa-miR-191, hsa-miR-200c, and hsa-let-7g. The nucleic acids in this aspect are capable of binding to a target nucleic acid molecule selected from the group consisting of hsa-miR-15b, hsa-miR-181b, hsa-miR-191, hsa-miR-200c, and hsa-let-7g. The nucleic acids are at least 5 nucleotides, at least 10 nucleotides, at least 15 nucleotides, at least 20 nucleotides, at least 25 nucleotides, at least 30 nucleotides or at least 40 nucleotides; and no longer than 25 nucleotides, no longer than 35 nucleotides; no longer than 50 nucleotides; no longer than 75 nucleotides, no longer than 100 nucleotides or no longer than 125 nucleotides in length.

The binding of the nucleic acid to the target nucleic acid is diagnostic for cancer, prognosticates an expected response to a cancer treatment, or prognosticates an expected survival of a subject having cancer.

The isolated nucleic acids can be associated with known diagnostic tools, such as DNA chips, RNA probes, or RNA primers.

The above-discussed embodiment and other aspects of the invention are further described by the experiments discussed below.

One embodiment of the aspects of the invention is a method, composition, kit or isolated nucleic acid for diagnosing a cancer. In this embodiment, if the expression of the microRNA in the sample is greater than the expression of the microRNA in the standard or control, then the increased expression of the microRNA indicates that the subject has cancer.

Another embodiment of the aspects of the invention is a method, composition, kit or isolated nucleic acid for prognosticating an expected response of a subject treated by a cancer treatment. In this embodiment, if the expression of the microRNA in the sample is greater than the expression of the microRNA in the standard or control, then the results indicate a poor or low prognosis for a subject to positively respond to the cancer treatment. Alternatively, if the expression of the microRNA in the sample is normal, approximately equal or equal to the expression of the microRNA in the standard or control, then the results indicate a good or high prognosis for a subject to positively respond to the cancer treatment. In this embodiment, a positive response is considered to be any of the following types of responses: total remission, partial remission, reduction in tumor size, or no change in the subject's disease progression. One non-limiting example is that if the amount of hsa-miR-181b is elevated, then the subject is less likely to positively respond to a cancer treatment; or, if the amount of hsa-miR-181b is normal, approximately equal or equal to the expression of hsa-miR-181b in the standard or control, then the subject is more likely to positively respond to the cancer treatment. Another non-limiting example is that if the amount of hsa-let-7g is elevated, then the subject is less likely to positively respond to a cancer treatment; or, if the amount of hsa-let-7g is normal, approximately equal or equal to the expression of hsa-let-7g in the standard or control, then the subject is more likely to positively respond to a cancer treatment. A positive prognosis for the expected effectiveness of the cancer treatment does not necessarily mean that a subject likewise has a positive prognosis for an expected survival of the cancer.

Thus, another embodiment of each the aspects is a method, composition, kit or isolated nucleic acid for prognosticating an expected survival of a subject having cancer. In this embodiment, if the expression of the microRNA in the sample is greater than the expression of the microRNA in the standard or control, then increased expression of the microRNA provides a poor or low prognosis for the subject to survive the cancer longer than a patient having cancer and normal expression levels of the microRNA or longer than the expectation for an average person having the particular cancer afflicting the subject. Alternatively, if the expression of the microRNA in the sample is normal, approximately equal or equal to the expression of the microRNA in the standard or control, then normal or approximately equal expression of the microRNA provides a good or high prognosis for the subject to survive the cancer longer than a patient having cancer and normal expression levels of the microRNA or longer than the expectation for an average person having the particular cancer afflicting the subject. One non-limiting example is that if the amount of hsa-miR-181b is elevated, then the subject is less likely to survive the cancer as compared to a person with the cancer who has normal levels of hsa-miR-181b, or to the expected survival of an average person having the cancer afflicting the subject. Another non-limiting example is that if the amount of hsa-miR-200c is elevated, then the subject is less likely to survive the cancer as compared to a person who has normal levels of hsa-miR-200c. The converse is also true. Thus, if the amount of hsa-miR-181b or hsa-miR-200c in the sample from a subject diagnosed with cancer is normal, approximately equal to or equal to the standard or control, then the subject has a positive prognosis for surviving the cancer, the subject is more likely to survive the cancer as compared to a subject with over-expressed hsa-miR-181b or hsa-miR-200c, or the subject is more likely to survive the cancer longer than an average person afflicted with the cancer. A positive prognosis of survival does not necessarily mean that a subject likewise is likely to have a positive response to a cancer treatment. However, if the sample contains normal levels of hsa-miR-181b, the subject then has a prognosis for a positive response to the cancer treatment and is more likely to survive the cancer or survive longer than a person with elevated levels of hsa-miR-181b.

Another embodiment of each of the aspects is a method, composition, kit or isolated nucleic acid wherein the increase in the expression of the microRNA is at least greater than 1 fold, at least greater than 1.4 fold, at least greater than 1.5 fold, or at least greater than 2 fold relative to the expression of the microRNA in the standard or control.

All aspects of the invention relate to the microRNA selected from the group consisting of hsa-miR-15b, hsa-miR-181b, hsa-miR-191, hsa-miR-200c, and hsa-let-7g. Alternatively, one embodiment of each aspect is that the microRNA is selected from the group consisting of hsa-miR-181b, hsa-miR-200c, and hsa-let-7g; is hsa-miR-181b; is hsa-miR-200c; or is hsa-let-7g.

The cancer treatment that the invention prognosticates is any cancer treatment known to a skilled artisan. Examples of expected responses to cancer treatments that are prognosticated by the claimed invention include, but are not limited to, chemotherapy, radiotherapy, and immunotherapy.

The experiments below are directed to colorectal cancer; however, it is believed that all other cancers can be diagnosed or prognosticated by the invention.

Experiment 1

Expression levels of ten microRNAs ("miRNA") were investigated to evaluate their clinical relevance in colorectal cancer. The ten miRNAs that were studied were: hsa-miR-30a-5p, hsa-miR-181b, hsa-let-7g, hsa-miR-26a, hsa-let-7b, hsa-miR-15b, hsa-miR-27a, hsa-miR-200c, hsa-miR-191 and hsa-miR-30c. Twenty-four normal and pair colorectal cancer specimens were selected as a model in this study. The results show that some of the miRNAs may function as oncogenes due to their over-expression in tumors. Over-expression of these miRNAs may be due to the loss of p53 tumor suppressor function in tumors.

Patients and Samples

A total of 48 snap frozen colorectal patient biopsy specimens were selected (24 pair normal and tumor specimens). These patients had undergone surgical resection of primary colorectal adenocarcinoma. The characteristics of these patients are shown in FIG. 1. Some were treated with adjuvant 5-FU based chemotherapy and others were treated with palliative high-dose 5-FU/FA.

RNA Isolation and cDNA Synthesis

Total RNAs were isolated using a method known within the art. In brief, TRIZOL® (Invitrogen, Calif.) was used to isolate total RNA from snap frozen tissues. RNA was treated with DNase I (Promega, Wis.). The integrity of the total RNA was determined by 1% formaldehyde-agarose gel. cDNA synthesis was carried out with the Superscript III cDNA synthesis kit (Invitrogen, Calif.) using 1 µg of total RNA as the template and specific reverse primers under 65° C. for 5 minutes and 50° C. for 60 minutes of reverse transcription. A total of three fragments were synthesized for further analysis.

Mutation Detection of p53 by PCR and Sequencing

The PCR reaction was carried out in a 25 µl reaction mixture containing cDNA 2 µl, 10×PCR golden buffer 2.5 µl, 1.5 mM MgCl2, 200 µM dNTP (Ambion, Tex.), 5 pmol primers and 1.25 U of AmpliTaq Gold polymerase plus 1M betaine (Sigma, Mich.). All PCR reagents were from Applied Biosystems Inc. except where mentioned. The reaction was initiated at 95° C. for 10 min. Thermal cycling was as follows: denaturing at 95° C. for 30 sec, annealing the primers using touchdown from 62° C. to 55° C. for 30 sec (0.5° C. decrement each round), extension at 72° C. for 35 seconds followed by an additional 25 rounds of 95° C. 30 sec, 55° C. 30 sec and 72° C. 40 sec. Final extension was carried out at 72° C. for 10 min on the PTC-225 Peltier Thermal Cycler (Bio-Rad, Mass.). PCR products were purified using a MultiScreen-PCR purifying plate (Millipore, Mass.) and submitted for sequencing. Sequencing was performed with the BigDye Terminator v3.1 Cycle Sequencing Kit from Applied Biosystems, Inc. (Calif.). Five microliters (50 ng) of template DNA was added to wells of a 96-well plate containing 15 µl of sequencing cocktail consisting of 0.4 µl premix from sequencing kit, 7.6 µl 2.5× sequencing buffer, 0.5 µl 10 mM primer and 6.5 µl water. Sequencing reactions were carried out for 35 cycles (96° C., 10 sec; 50° C., 5 sec; 60° C., 2 min 30 sec). The products were precipitated with 50 µl 100% ethanol and 2 µl 3M NaOAc (pH 4.8), and pellets were rinsed with 70% ethanol. After addition of 10 µl Hi-Di Formamide (Applied Biosystems Inc, Calif.) and denaturing at 94° C. for 10 min, samples were loaded onto an ABI 3730x1 sequencer. Sequences were analyzed with SeqManII from DNASTAR, Inc. by comparing with Homo sapiens tumor protein p53 mRNA sequence to normal p53 mRNA. All allelic variations were recorded.

miRNA Reverse Transcription and qRT-PCR Analysis mirVana™ qRT-PCR Primer Sets (Ambion Inc. Tex.) for miRNA specific reverse transcription including hsa-miR-30a-5p, hsa-miR-181b, hsa-let-7g, hsamiR-26a, hsa-let-7b, has-miR-15b, has-miR-27a, has-miR-200c, has-miR-191, has-miR-30c, and endogenous control 5S rRNA were utilized according to the manufacture's protocol. Briefly, the reaction master mix containing mirVana™ 5× RT Buffer, 1×mir'Vana™ RT Primer, Array-Script™ Enzyme Mix and nuclease-free water was mixed with 20 ng of each total RNA sample. These mixtures were incubated for 30 min at 37° C., then 10 min at 95° C. qRT-PCR was carried out using the Applied Biosystems 7500 Real-Time PCR System (Applied Biosystems Inc. Calif.) and mirVana™ qRT-PCR miRNA Detection Kit (Ambion Inc. Tex.). The PCR master mix containing mirVana™ 5×PCR Buffer (with SYBR® Green I), 50×ROX, SuperTaq™ Polymerase, mirVana™ PCR Primers, and RT products was processed as follows: 95° C. for 3 min, and then 95° C. for 15 sec, 60° C. for 35 sec for up to 40 cycles (n=3). Signal was collected at the endpoint of every cycle.

Statistical Analysis

The gene expression ACT values of miRNAs from each sample were calculated by normalizing with internal control 5S rRNA and relative quantization values were plotted. The statistically significant differences in expression level between tumor and normal tissues for each target were calculated using a paired Wilcoxon test. The Log-rank test for the generated Kaplan-Meier curve was conducted to evaluate the association between the expression level of each miRNA and survival rate. The cut-off was set to p<0.05.

Results

Over-Expression of miRNA in Cancer

Figure 3:
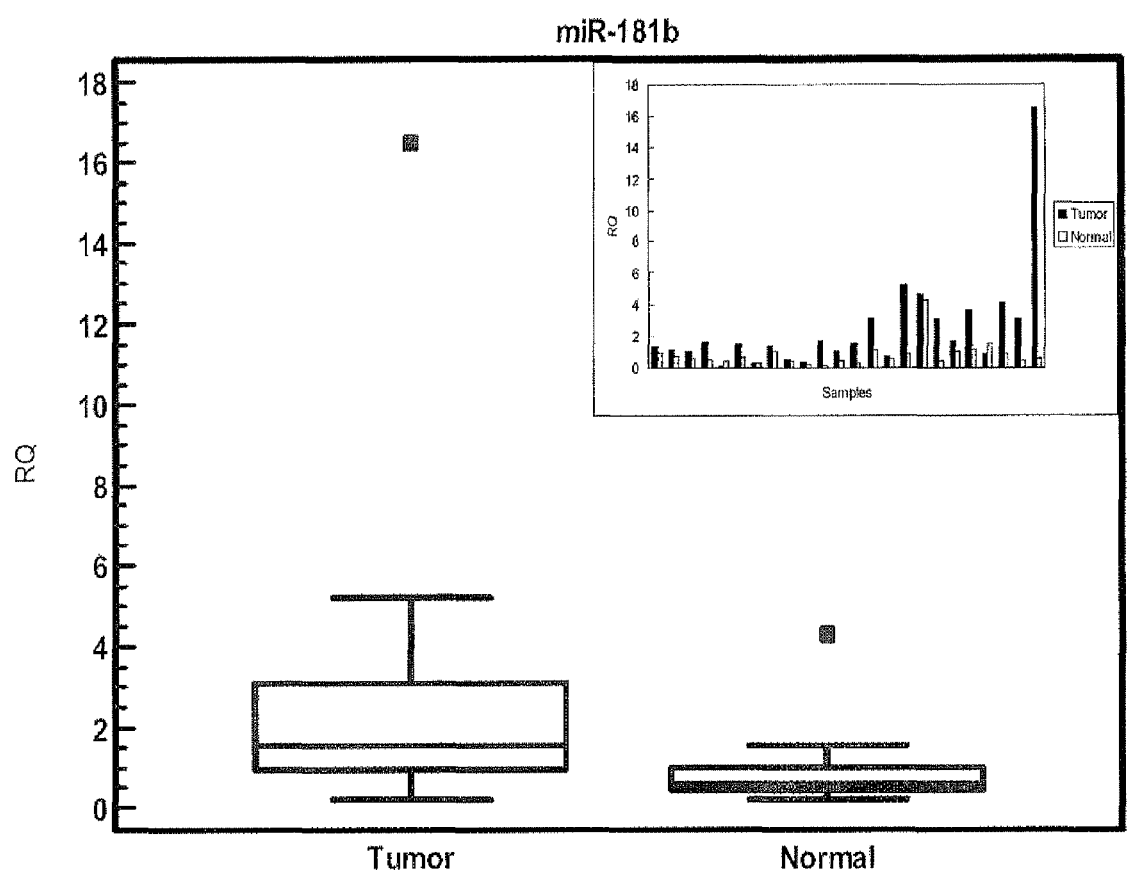
FIG. 3 is a graph depicting the levels of hsa-miR-181b in cancer cells and normal cells obtained from the patients studied in Experiment 1. The small chart contained within the graph displays the microRNA expression for all individual paired samples.
Figure 4:
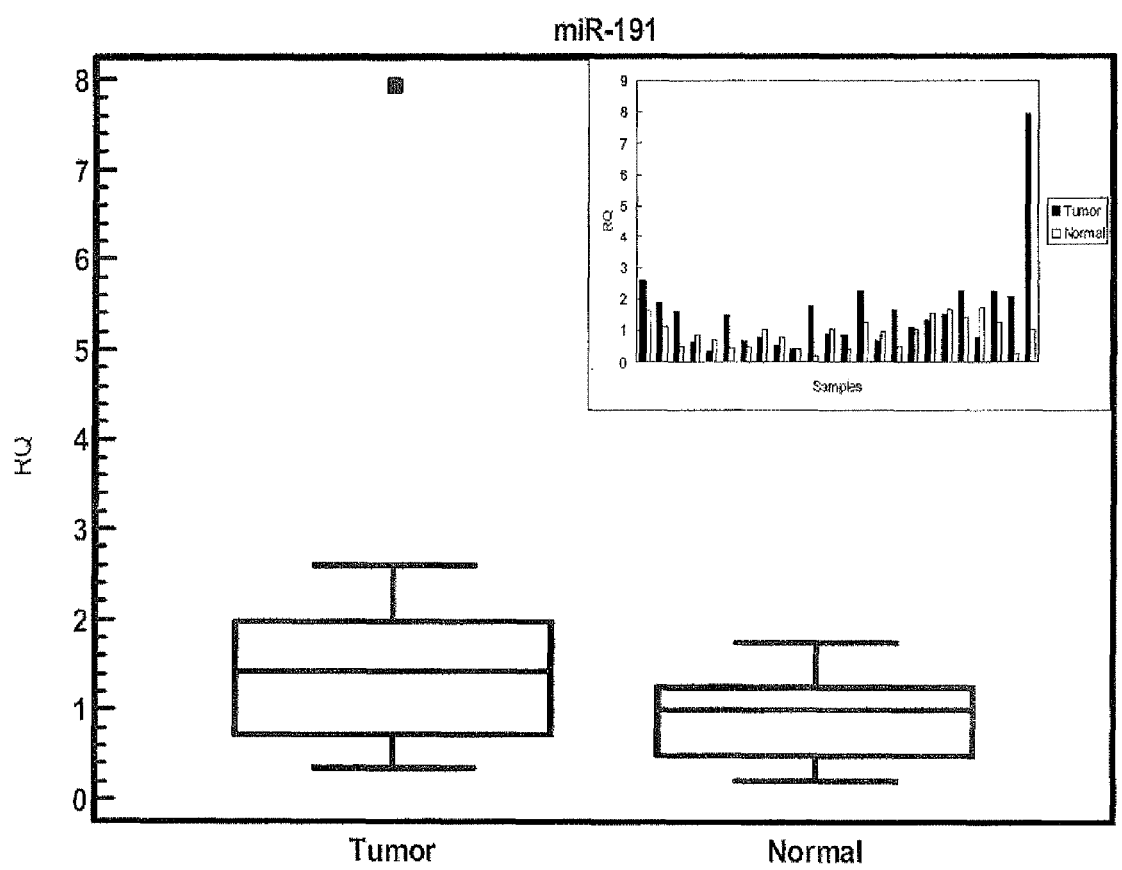
FIG. 4 is a graph depicting the levels of hsa-miR-191 in cancer cells and normal cells obtained from the patients studied in Experiment 1. The small chart contained within the graph displays the microRNA expression for all individual paired samples.
Figure 5:
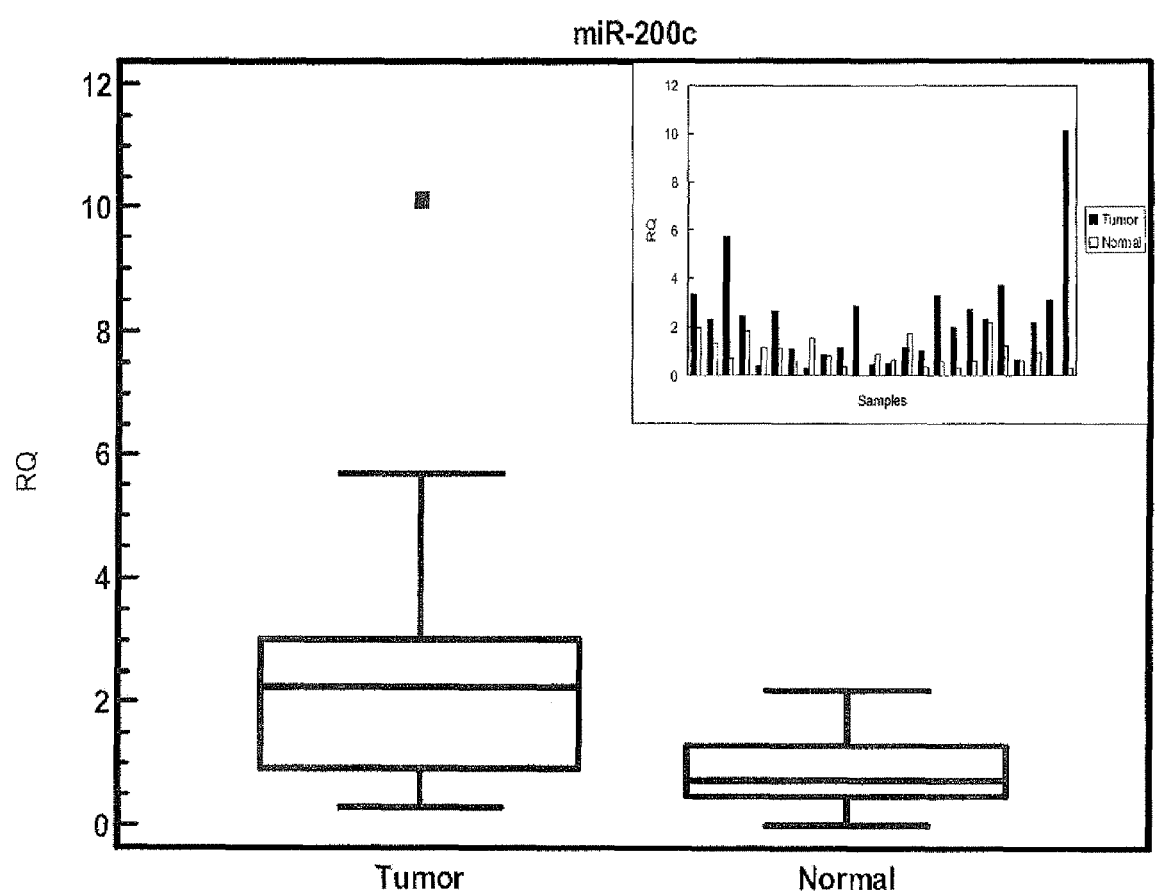
FIG. 5 is a graph depicting the levels of hsa-miR-200c in cancer cells and normal cells obtained from the patients studied in Experiment 1. The small chart contained within the graph displays the microRNA expression for all individual paired samples.

In this study, the expression levels of 10 different miRNAs known to be deregulated based on our previous studies were quantified using miRNA specific qRT-PCR analysis. Among these, four miRNAs were found to be over-expressed in colorectal cancer samples. The expression of hsa-miR-15b was over-expressed by nearly 1.5-fold (Median: 130 vs. 0.89, p=0.0278) (FIG. 2). The expression of hsa-miR-181b was elevated 2.5-fold (Median: 1.54 vs. 0.61, p=0.0002) in tumor samples (FIG. 3). The expression of hsa-miR-191 was enhanced 1.4-fold (Median: 1.44 vs. 1.01, p=0.0264) in colorectal tumors (FIG. 4). The expression of hsa-miR-200c was also up-regulated 3-fold in tumor specimens (Median: 2.25 vs. 0.75, p=0.0017) (FIG. 5).

Evaluation of Prognostic Values of miRNAs

Figure 6:
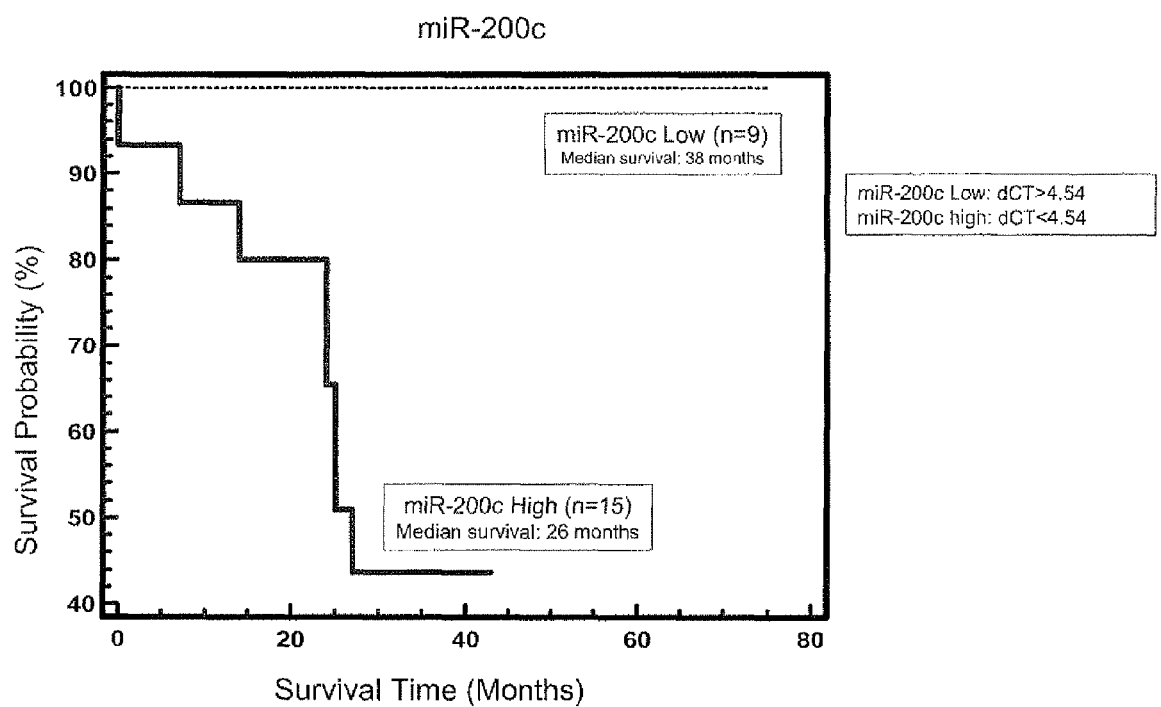
FIG. 6 is a Kaplan-Meier overall survival curve relative to the expression of hsa-miR-200c.

To further evaluate the clinical relevance of these over-expressed miRNAs in colorectal cancer in terms of prognosis, Kaplan-Meier survival analysis was performed using patient overall survival. Our results indicated that hsa-miR-200c was significantly associated with patient survival (FIG. 6). Patients (n=9) with low expression of hsa-miR-200c (ΔCT less than 4.54) tended to have longer survival (median survival of 38 months vs. 26 months) than patients (n=15) with higher levels of hsa-miR-200c expression (p=0.00122). The expression of hsa-miR-200c was not related to the difference in tumor stage.

Figure 7:
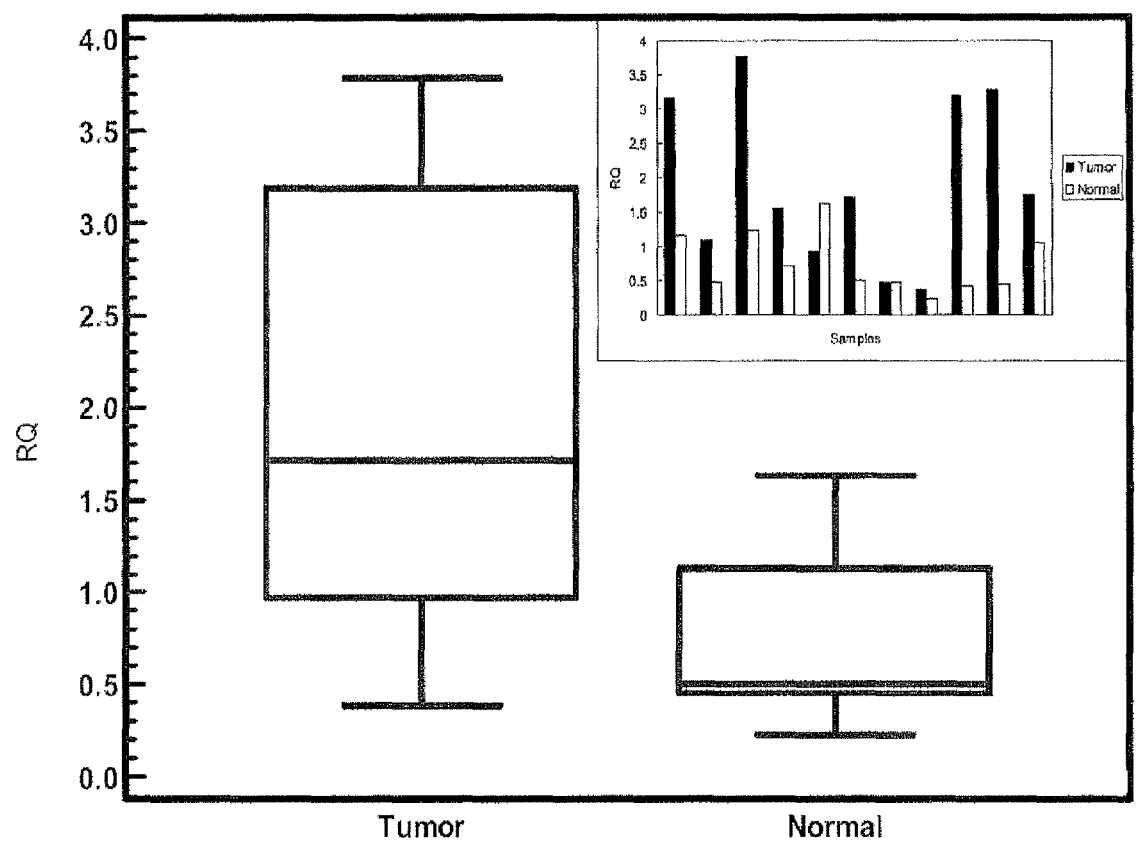
FIG. 7 is a graph showing the expression if hsa-miR-181b in cancer cells with mutated p53 and normal cells.
Figure 8:
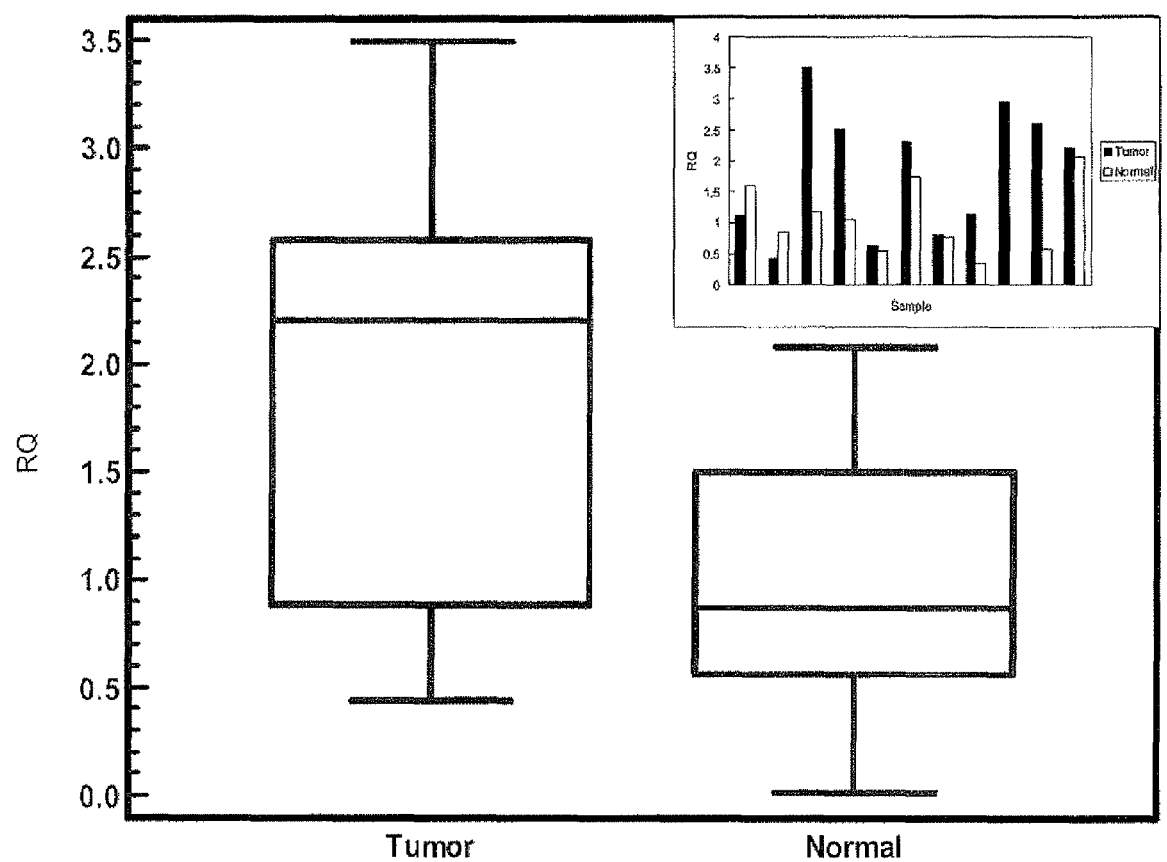
FIG. 8 is a graph showing the expression if hsa-miR-200c in cancer cells with mutated p53 and normal cells.

It was also discovered that over 46% of colorectal tumors contained p53 mutations or deletions (Table 1). Representative p53 sequence traces around the mutation and deletion regions are illustrated in FIG. 3. The expression of hsa-miR-181b was 3.4-fold higher in 11 tumors with p53 mutations/deletions than the corresponding normal samples with wild type p53 and was strongly associated with p53 mutation status (median: 1.72 vs. 0.50, p=0.0098) (FIG. 7). The expression of hsa-miR-200c was 2.5-fold higher in the 11 tumors containing p53 deletions/mutations than the corresponding counterparts and was also strongly associated with the p53 mutation status (median: 2.20 vs. 0.87, p=0.03) (FIG. 8). We also compared the expression status of miRNAs within the tumors with or without p53 mutations. The results also showed a significant correlation of hsa-miR-200c and hsa-miR-181b with p53 mutation status. Both, of these miRNAs contain p53 binding site(s) in the putative promoter regions.

TABLE 1 p53 Mutations Confirmed by cDNA Sequencing

| Sample | cDNA-Position | Normal Sequence | Tumor Sequence | Normal translated Peptide | Tumor Translated Peptide |
|---|---|---|---|---|---|
| 15 | 720 | GTC | TTC | Leu | Ser |
| 25 | 766 | GTT/GAT | GAT | Val/Asp | Asp |
| 09 | 775 | CCC | CAG | Arg | Gln |
| 26 | 829 | CAT | CGT | His | Arg |
| 07 | 835 | ATC | ACC | Ile | Thr |

TABLE 1-continued p53 Mutations Confirmed by cDNA Sequencing

| Sample | cDNA-Position | Normal Sequence | Tumor Sequence | Normal translated Peptide | Tumor Translated Peptide |
|---|---|---|---|---|---|
| 12 | 859 | GTG | GTG/GAG | Val | Val/Glu |
| 13 | 984 | GGC | AGC | Gly | Ser |
| 29 | 984 | GGC | AGC | Gly | Ser |
| 22 | 1084 | CCT | CTT | Pro | Leu |
| 23 | 1167 | CGA | CGA/TGA | Arg | Arg/Ter(Stop) |
| 17 | 626-646 | | Deleted | | Deleted |

Discussion

Many recent efforts in the field of cancer research have focused on miRNA biology. Even a small change in miRNA expression can cause a profound effect on the gene expression of hundreds of mRNAs at the post-transcriptional or translational level. Mounting evidence has shown that miRNAs are involved in cancers such as lymphoblastic leukemia, glioblastoma, B-cell chronic lymphocytic leukemia (B-CLL), and many solid tumors including colon cancer (Benard and Douc-Rasy, 2005; Cahn et al. 2004; Cimmino et al. 2005; Cummins et al. 2006). Thus, it is believed that the expression levels of hsa-miR-15b, hsa-miR-181b, hsa-miR-191, hsa-miR-200c, or hsa-let-7g can be used to diagnose patients. Additionally, the expression level of these miRNAs can also be used to predict a response that a patient will have to a cancer treatment, or predict the survival of the patient. These over-expressed miRNAs may be involved in the oncogenic process.

Four of the ten miRNAs were over-expressed in colorectal cancer samples (FIG. 2, FIG. 3, FIG. 4 and FIG. 5). Each of these miRNAs is capable of potentially regulating well over 100 target mRNAs via imperfect base pairing, some of which may be oncogenes. The hsa-miR-200c is additionally associated with overall patient survival, (FIG. 6). hsa-miR-200c can potentially regulate over 200 target genes including MAP-KKK3, eIF-4E, RAS homologs, RNA polymerase II, and cyclin L1 based on bioinformatics analysis (John et al. 2004). Thus, in some way, miRNAs can be viewed as master regulators.

The p53 status in these samples was determined via sequencing of the p53 cDNAs (Table 1). Nearly 50% of the tumors contained p53 mutations/deletions. Among the tumors with mutated p53, both hsa-miR-181b (FIG. 7) and hsa-miR-200c (FIG. 8) were highly over-expressed compared to the paired normal samples. The loss of p53 tumor suppressor function will activate some of these potential oncogenic miRNAs. Many genes such as cytochrome C, ECIP-1, MAPPKKK1, TEM6, E2F5, GATA6, PP2B, and eIF5A, are predicted to be regulated by hsa-miR-181b. These genes have been shown to be important for cell signaling, cell cycle control and chemo-sensitivity. It is believed that the miRNAs can modulate expression of a number of genes at the translational level.

In conclusion, the in vivo significance of ten mature miRNAs was evaluated in 24 matched normal and colorectal cancer patient samples. The expression of hsa-miR-15b, hsa-miR-181b, hsa-miR-191 and hsa-miR-200c were significantly over-expressed in colorectal cancer patients and they may be associated with the development of the disease. The expression of hsa-miR-200c was strongly associated with overall patient survival. That expression of hsa-miR-200c was not related to the different stages of the disease further supports this notion.

Experiment 2

Experiment 1 identified a number of deregulated miRNAs due to the loss of p53 tumor suppressor in colon cancer cell lines. To further investigate the in vivo biological significance of these miRNAs, the expression of hsa-let-7g, hsa-miR-143, hsa-miR-145, hsa-miR-181b and hsa-miR-200c were investigated using formalin-fixed paraffin embedded colon cancer specimens to evaluate the potential relationship with chemo-sensitivity and tumorigensis.

Patients and Methods

Paraffin sections of the colorectal cancer samples were obtained from 46 patients. These patients had undergone surgical removal from 1996 to 2002. Among the 46 patients, 21 normal samples were also obtained. Patients who had recurrence or residual colorectal cancer lesions were treated with S-1 alone or S-1 plus cisplatin (CDDP). The dose of S-1 was determined based on the patient's body surface area ("BSA") as follows: BSA<1.25 $m^2$, 80 mg/day; BSA$\geq$1.25 $m^2$ and BSA<1.5 $m^2$, 100 mg/day; BSA>1.5 $m^2$, 120 mg/day. The regimen of the treatment was the following: S-1 alone-S-1 wad administered twice a day orally for 28 consecutive days, followed by a two-week drug-free interval; and S-1/CDDP-S-1 was administered twice a day via oral administration followed by two weeks S-1 free interval, while CDDP (30 mg/$m^2$) was injected intravenously on day 1 and 8.

The archived colorectal cancer FFPE specimens (contained either >90% tumor or >90% normal tissue) were dissected and placed in nuclease-free micro-centrifuge tubes. The deparaffinization was performed by adding 1 ml of Xylene and vortexing for five minutes at room temperature. The samples were incubated for three minutes at 60° C. After incubation, the samples were centrifuged at 14,000 rpm for seven minutes at room temperature. The supernatants were removed and 1 ml of 100% ethanol was added with vortexing for seven minutes at room temperature. After the supernatant was removed, the ethanol washes were repeated. After centrifugation, the samples were air dried and 180 μl of digestion buffer (30 mM Tris-HCl, 20 mM EDTA, 1% SFS and nuclease-free water) were added to the samples followed by homogenization. After homogenization, 20 μl of Proteinase K (QIAGEN Inc., Valencia, Calif.) solution were added and the samples were incubated for an additional three hours at 56° C. Subsequently, 500 μl of TRIZOL® were added and followed by vortexing for five minutes at room temperature. 50 μl of 1-bromo-3-chloropropane ("BCP") salutation was added and vortexed for two minutes. The samples were incubated for three minutes at room temperature. After centrifugation at 14,000 rpm for seven minutes at 4° C., the upper aqueous phase containing extracted RNA was transferred to a new micro-centrifuge tube. 100 µg of glycogen were added and mixed by vortexing. The samples were precipitated with 500µ of 100% isopropanol and were incubated for 60 minutes at −20° C. The RNA samples were centrifuged at 14,000 rpm for seven minutes at 4° C. After removing the supernatant, 1 ml of 75% ethanol was added and the samples were centrifuged at 14,000 rpm for seven minutes at 4° C. Upon removal of the supernatant, the RNA pellet was air dried and re-suspended in nuclease-free water.

qRT-PCR Primer Sets (Ambion, Inc, Austin, Tex.) for hsa-let-7g, hsa-miR-143, hsa-miR-145, hsa-miR-200c and 5S ribosomal RNA as an internal control specific reverse transcription were utilized based on the manufactures' protocol. Quantitative real-time PCR was carried out using 7500 Real-Time PCR System (Applied Biosystems, Inc). For hsa-let-7g, hsa-miR-143, hsa-miR-145 and hsa-miR-200c, the PCR master mix of a total reaction volume of 25 µl for each reaction containing mirVana™ (Ambion, Inc., Austin, Tex.) 5×PCR Buffer (with SYBR® Green I), 50×ROX, Super-Taq™ Polymerase, mirVana™ PCR Primers for each target, nuclease0 free water and RT products were prepared. The PCR conditions were as follows: 95° C. for three minutes, followed by 40 cycles of 95° C. for 15 seconds and 60° C. for 35 seconds. For hsa-miR-181b, the PCR master mix of total reaction volume of 20 µl for each reaction containing TAQ-MAN® 2× Universal PCR Master Mix (No AmpErase UNG), hsa-miR-181b and RNU6B 10× TAQMAN® Assay, nuclease-free water and 1.33 µl of RT products were prepared. PCR conditions were as follows: 95° C. for ten minutes, followed by 40 cycles of 95° C. for 15 seconds and 60° C. for 35 seconds.

Expression levels of each miRNA were normalized by calculating the $\Delta C_T$ value based on subtracting the $C_T$ value of the target miRNA from the $C_T$ value of the internal control 5S rRNA or RNU6B. The sample with the highest expression levels of miRNAs set the upper limit to generate relative expression values for the other of the samples. The statistical differences of the expression levels between tumor and normal tissues for each target miRNA were calculated by the Wilcoxon test. The Mann-Whitney test was performed for comparison of the chemo-response data for hsa-let-7g and hsa-miR-181b. The Log-rank test for Kaplan-Meier curve was generated to evaluate the association between the expression of each miRNA and the survival rate. Statistical significance was set as a $p \leq 0.05$.

Results

Figure 9:
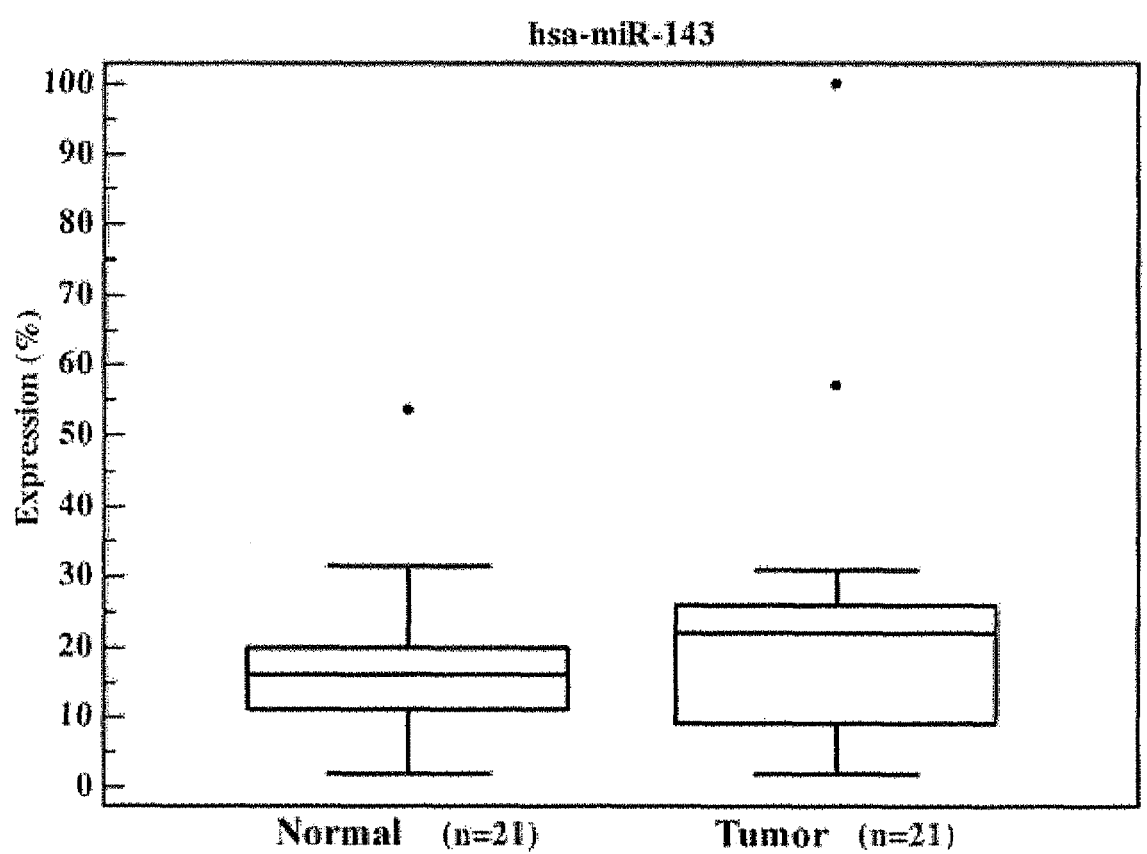
FIG. 9 is a graph depicting the levels of hsa-miR-143 in cancer cells and normal cells obtained from the patients studied in Experiment 2.
Figure 10:
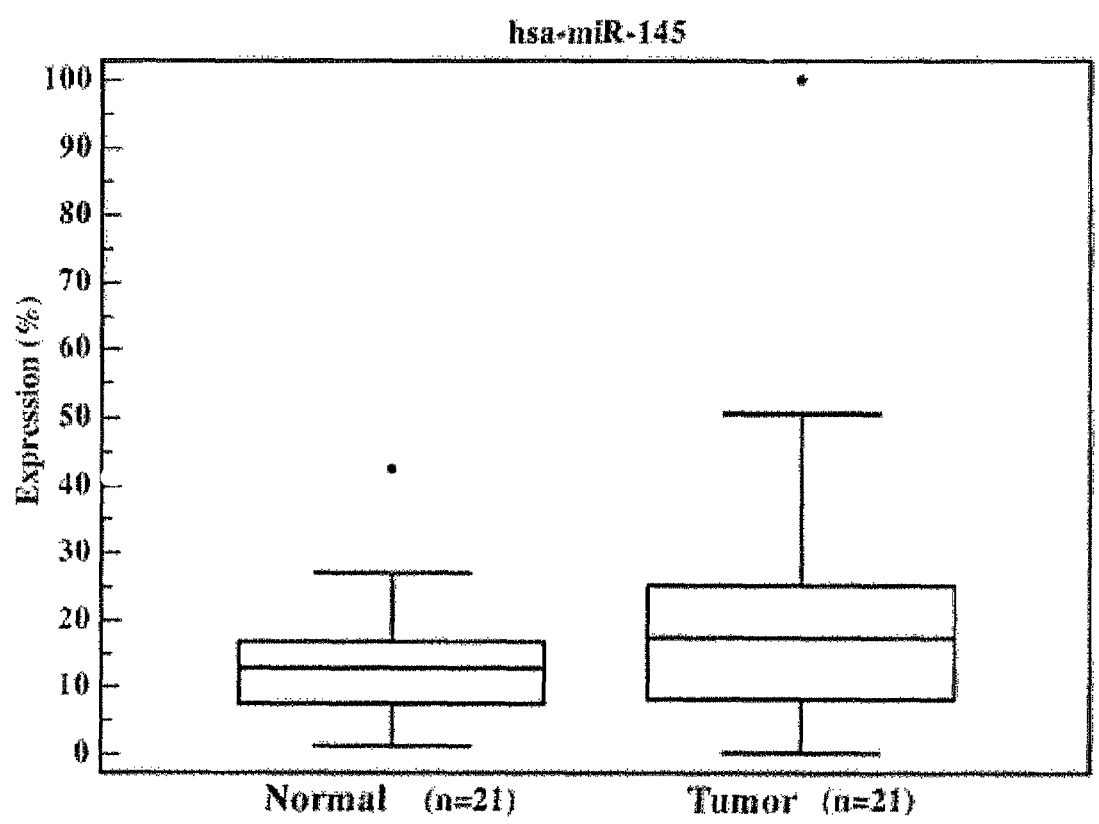
FIG. 10 is a graph depicting the levels of hsa-miR-145 in cancer cells and normal cells obtained from the patients studied in Experiment 2.
Figure 11:
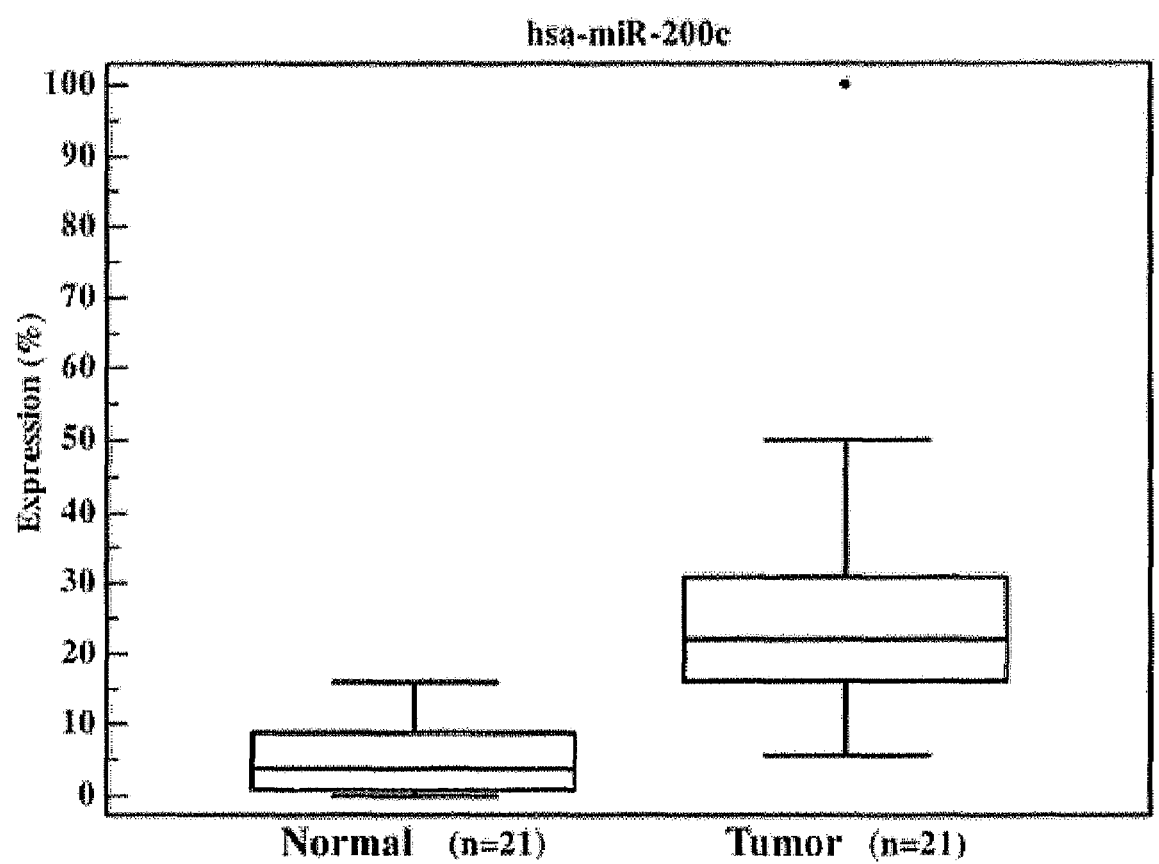
FIG. 11 is a graph depicting the levels of hsa-miR-200c in cancer cells and normal cells obtained from the patients studied in Experiment 2.
Figure 12:
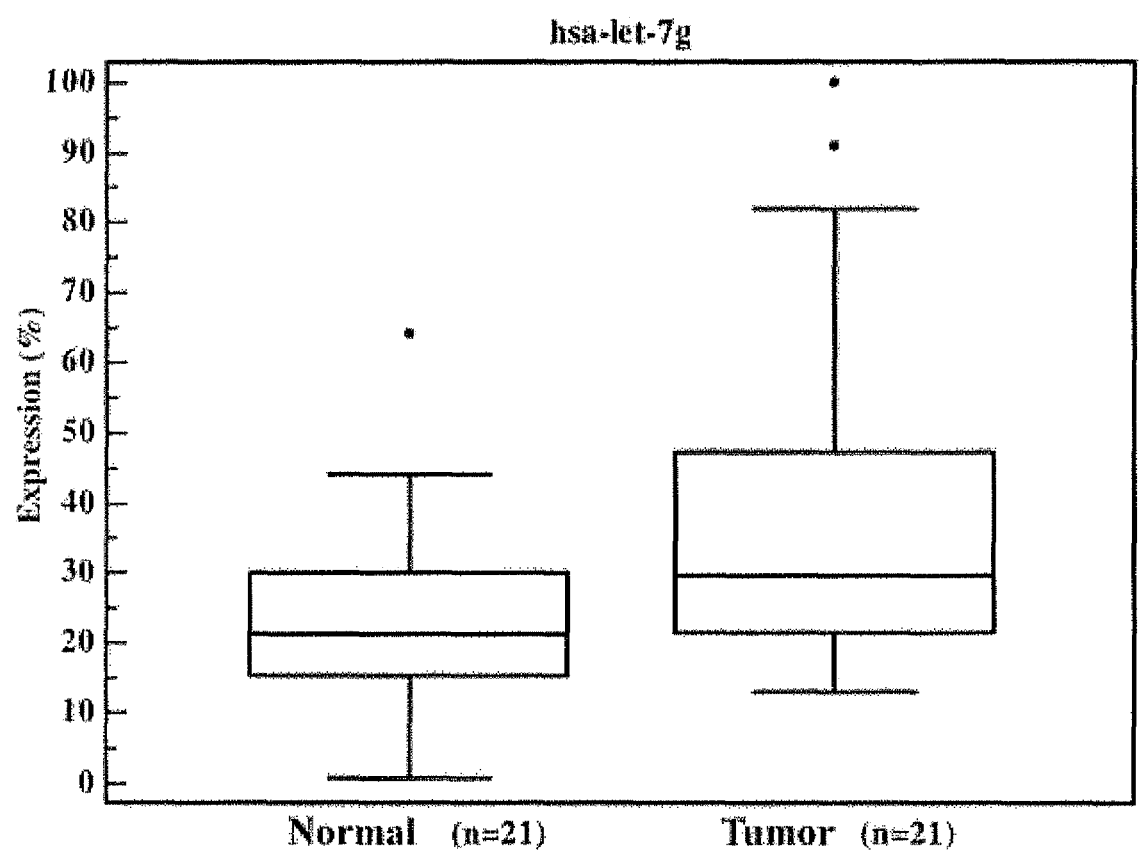
FIG. 12 is a graph depicting the levels of hsa-let-7g in cancer cells and normal cells obtained from the patients studied in Experiment 2.
Figure 13:
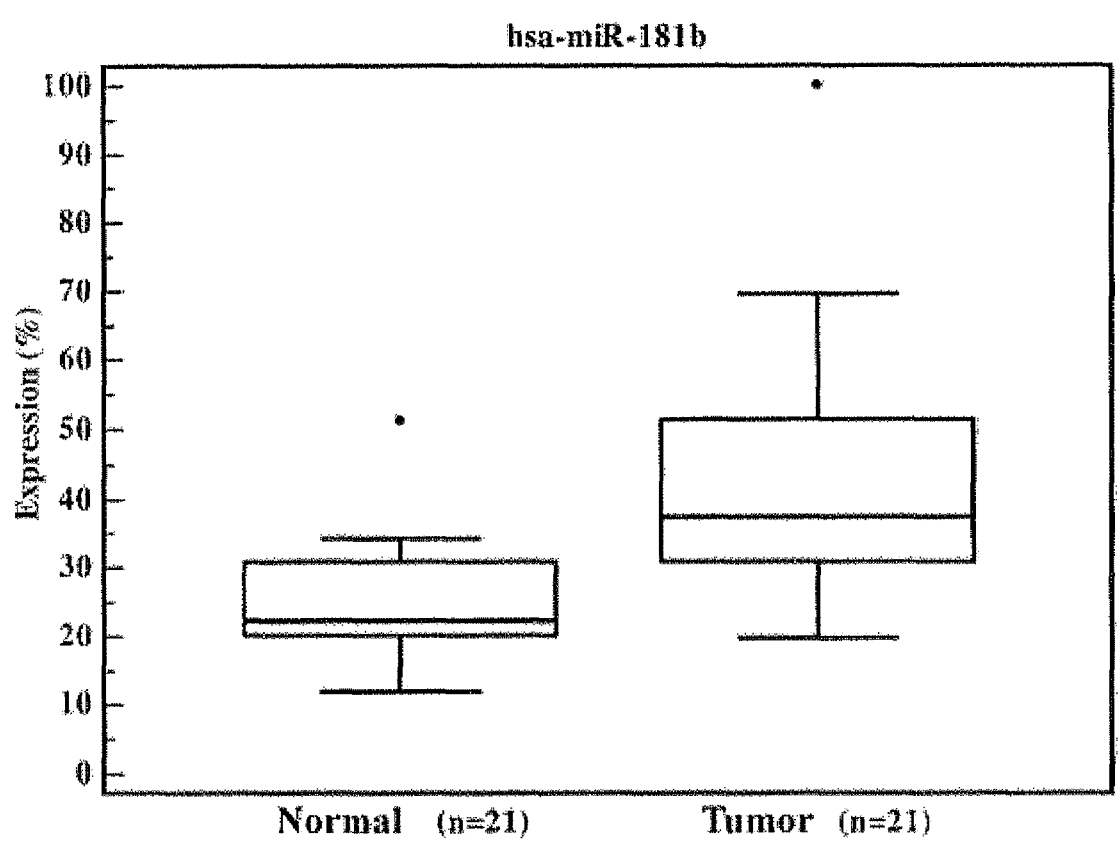
FIG. 13 is a graph depicting the levels of hsa-miR-181b in cancer cells and normal cells obtained from the patients studied in Experiment 2.

The tumor tissues from 46 patients were divided into a response group (n=27, including the patients evaluated as complete remission, partial response and stale disease after treatment with S-1) and a disease progression patient group (n=19) according to their response to S-1 treatment. The expression levels of five mature miRNAs in these samples were screened via miRNA specific real time qRT-PCR analysis. Based on the real time qRT-PCR analysis, there was no significant difference in expression levels of hsa-miR-143 (FIG. 9) and hsa-miR-145 (FIG. 10) between tumor tissues and corresponding normal samples (p=0.1219 and 0.0853 respectively). In contrast, the expression level of hsa-miR-200c was significantly over-expressed by nearly 6-fold in tumor tissues compared to the corresponding normal samples (p=0.0001) (FIG. 11). Hsa-let-7g was also significantly over-expressed in tumor tissues compared to corresponding normal colorectal samples (p=0.0037) (FIG. 12). The expression level of hsa-miR-181b was elevated in tumors compared to the corresponding normal samples (p=0.0005) (FIG. 13).

Figure 14:
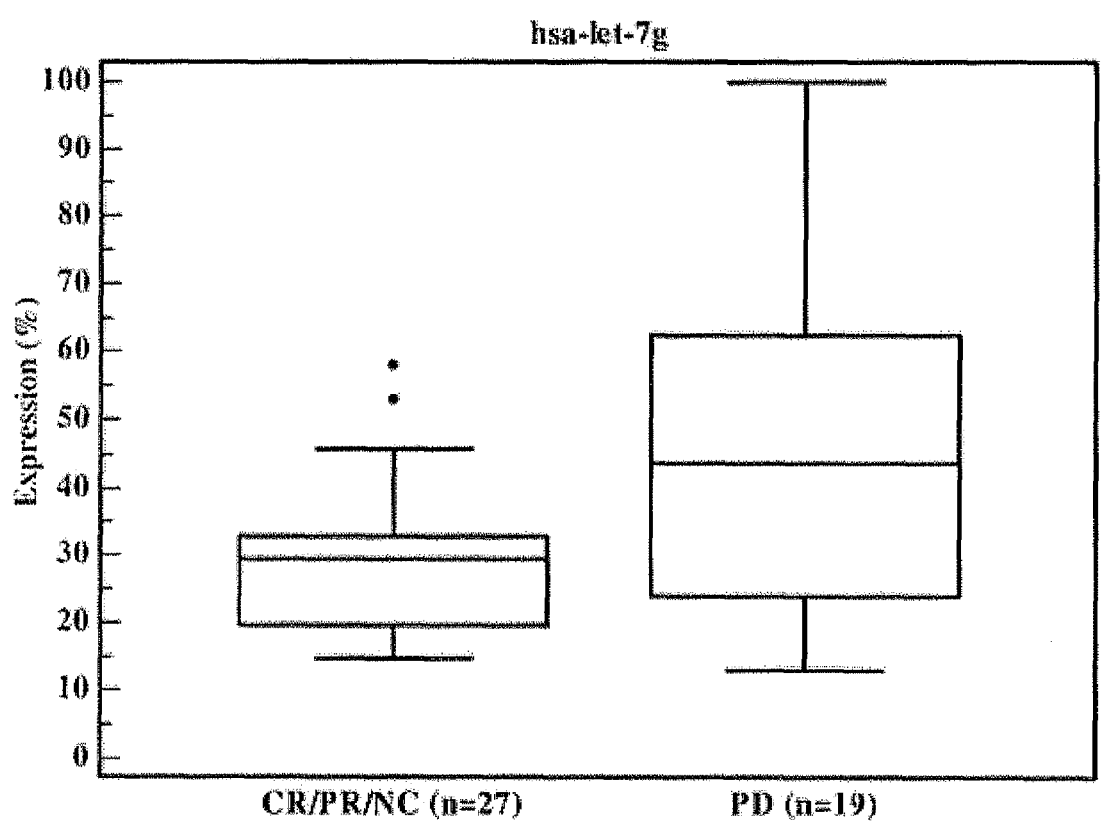
FIG. 14 is a graph depicting the response of a patient to S-1 treatment relative to hsa-let-7g expression.
Figure 15:
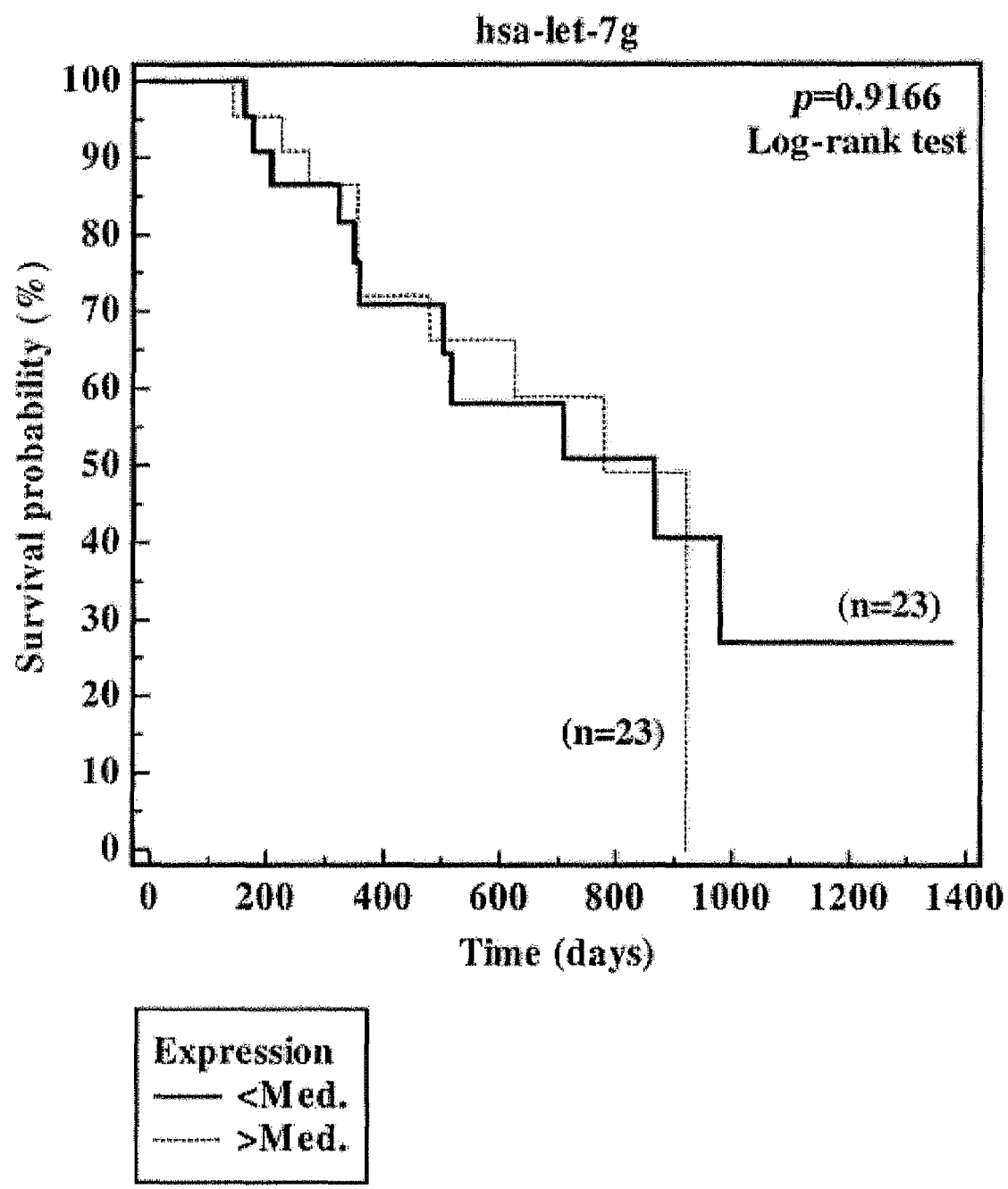
FIG. 15 is a Kaplan-Meier overall survival curve relative to hsa-let-7g expression.
Figure 16:
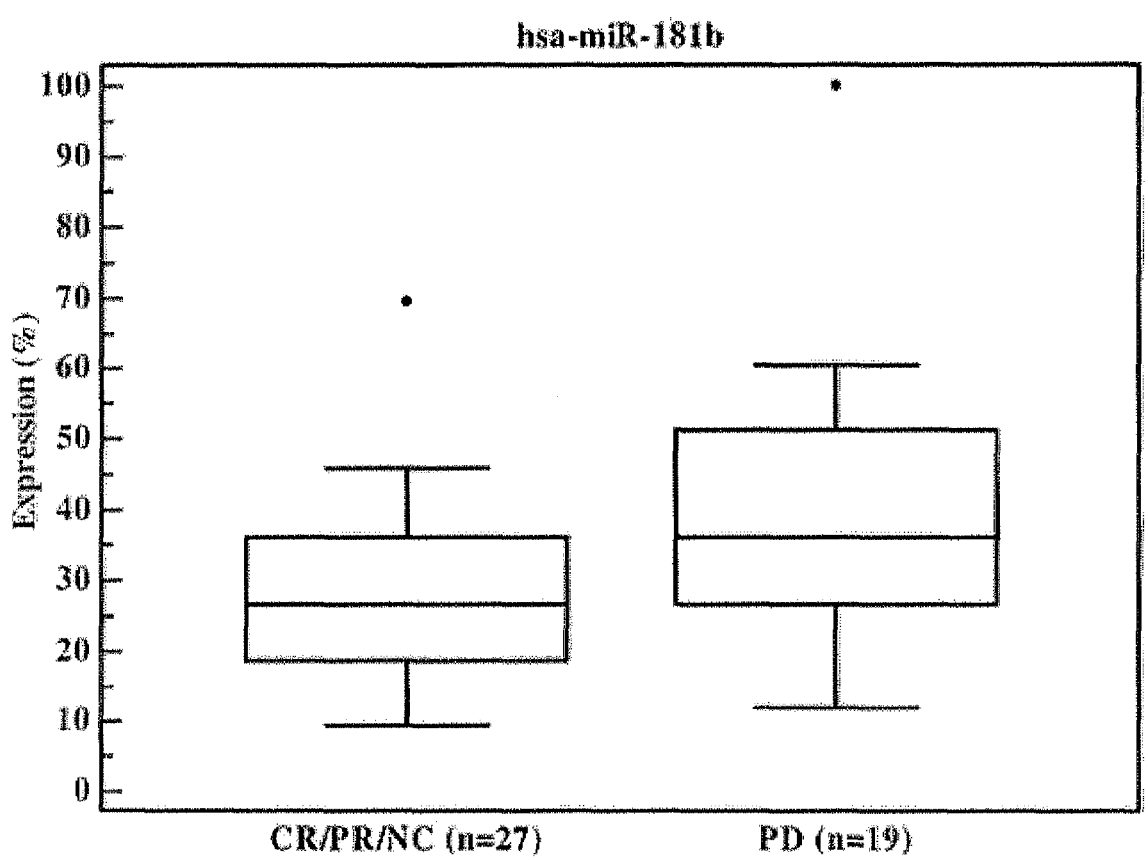
FIG. 16 is a graph depicting the response of a patient to S-1 treatment relative to hsa-miR-181b expression.
Figure 17:
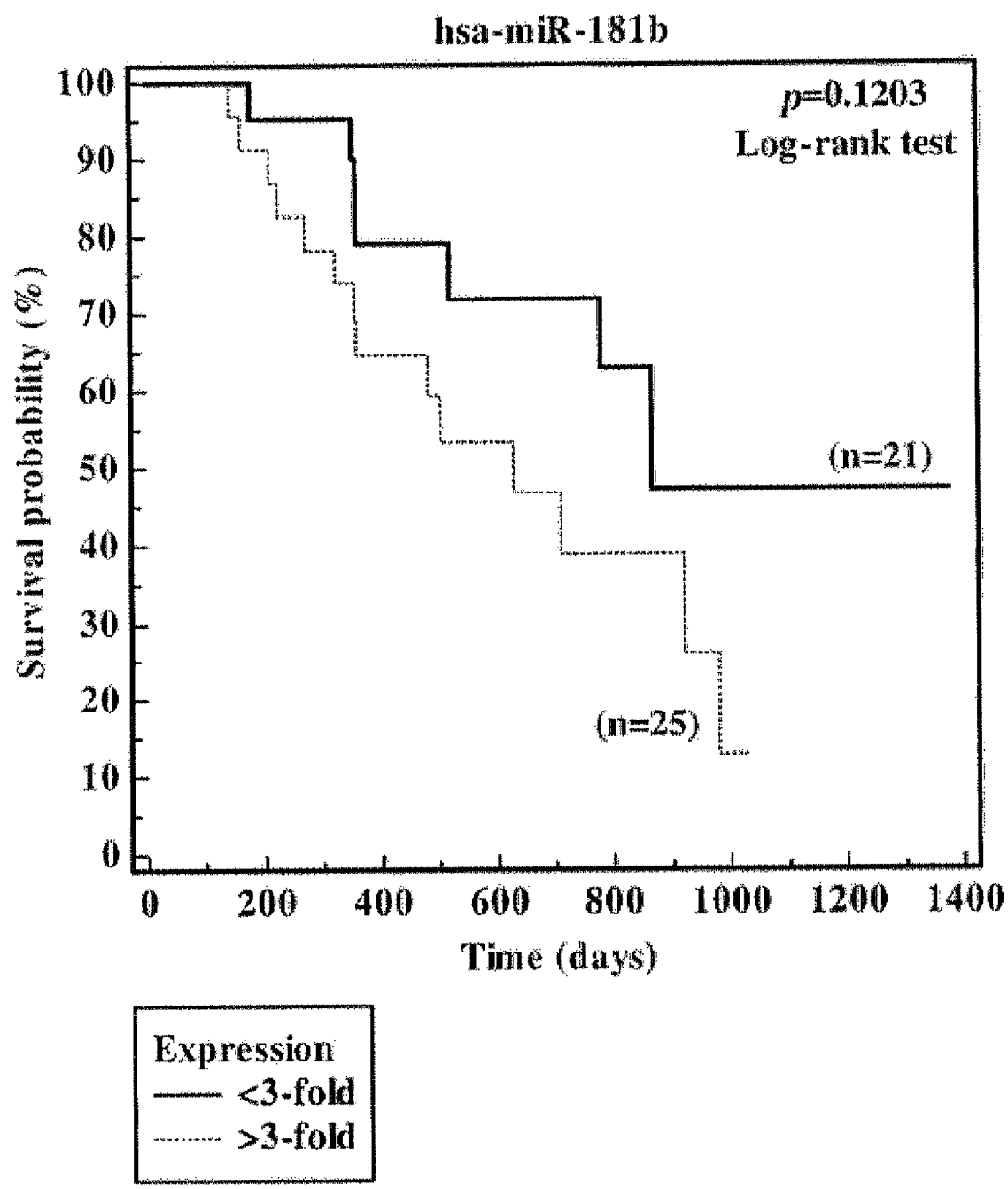
FIG. 17 is a Kaplan-Meier overall survival curve relative to hsa-miR-181b expression.

To evaluate the potential association of certain miRNAs with patient clinical response, the expression levels of each miRNA in the response group was compared to the levels in patients with disease progression. Patients who responded to S-1 treatment tend to have lower expression level of hsa-let-7g compared to the disease progression group (p=0.0305) (FIG. 14). However, the expression of hsa-let-7g was not associated with better survival based on the Kaplan-Meier survival analysis (p=0.9166) (FIG. 15). On the other hand, the expression of hsa-miR-181b was strongly associated with patient response. Patients who responded to S-1 treatment also displayed a lower expression level of hsa-miR-181b compared to the disease progression group (p=0.0209) (FIG. 16). However, this parameter was not associated with patient survival based on Kaplan-Meier survival analysis (p=0.1203) (FIG. 17).

Discussion

The expression level of hsa-miR-200c was significantly over-expressed in the colorectal tumor samples compared to the corresponding normal samples. The expression of hsa-let-7g was significantly over-expressed in colorectal cancer samples compared to the corresponding normal samples. The over-expression of hsa-let-7g was indicative of poor response to chemotherapeutic sensitivity of S-1. This may be due to the hsa-let-7g mediated target transcripts such as E2F, cyclin D and c-myc. Although expression levels of hsa-let-7g were significantly associated with a patient's response to S-1 (FIG. 14), there was no discernible benefit in predicting patient survival (FIG. 15).

The expression of hsa-miR-181b was significantly associated with a patient's response to S-1 treatment, such as fluoropyrimidine based drugs. Many genes, such as cytochrome C, ECIP-1, MAPPKKK1, TEM6, E2F5, GATA6, PP2B and eIF5A may be regulated by hsa-miR-181b. These genes may modulate in response to hsa-miR-181b expression levels, and may affect cell cycle control and chemo-sensitivity. Although hsa-miR-181b is associated with a patient's clinical response to chemotherapy (FIG. 16), the expression if hsa-miR-181b was not a significant predictor of a patient's survival (FIG. 17).

CONCLUSION

The experiments discussed above relate to detecting and diagnosing cancer, prognosticating the expected response and the expected survival of a subject afflicted with colorectal cancer, and indicate the presence of pre-cancerous lesions.

These microRNAs are also tools for diagnosing cancer. Since these microRNAs interact with critical cell cycle genes, it is expected that the over-expression of these microRNAs will precede any other biomarker currently used or available to diagnose cancer. Therefore, the detection of over-expression of hsa-miR-15b, hsa-miR-181b, hsa-miR-191, hsa-miR-200c, or hsa-let-7g is expected to be diagnostic for cancer.

Although the present invention has been described in considerable detail with reference to preferred embodiments thereof, other embodiments are possible for those skilled in the art and various modifications and variations can be made to the present invention without departing from the scope or spirit of the invention. In view of the foregoing, it is intended that the present invention cover modifications and variations of this invention provided they fall within the scope of the following claims and their equivalents. It is therefore intended that this invention be limited only as indicated by the appended claims.

What is claimed is:

1. A method of detecting or diagnosing a cancer comprising the steps of:
    obtaining a biological sample from a subject in need of diagnosis;
    measuring an amount of a first microRNA in the biological sample selected from the group consisting of: hsa-miR-15b, hsa-miR-181b, hsa-miR-200c, and hsa-let-7g;
    measuring an amount of a second microRNA in the biological sample selected from the group consisting of hsa-miR-15b, hsa-miR-181b, hsa-miR-200c and hsa-let-7g, wherein the second microRNA is different from the first microRNA;
    comparing the amount of the first microRNA and the second microRNA found in the biological sample to a standard amount of the first microRNA and the second microRNA found in normal or non-cancerous cells or to an amount of the first microRNA and the second microRNA in a control sample,
    wherein the presence of an amplification in the amount of the first microRNA and the second microRNA found in the sample relative to the standard or the control is diagnostic for the presence of cancer;
    wherein the absence of an amplification in the amount of the first microRNA and the second microRNA found in the sample relative to the standard or control is diagnostic for the absence of cancer; and
    wherein the cancer is colorectal cancer.

2. The method according to claim 1, wherein the first microRNA is further selected from the group consisting of: hsa-miR-181b, hsa-miR-200c, and hsa-let-7g.

3. The method according to claim 1, wherein the first microRNA is hsa-miR-181b.

4. The method according to claim 1, wherein the first microRNA is hsa-miR-200c.

5. The method according to claim 1, wherein the first microRNA is hsa-let-7g.

6. The method according to claim 1 further comprising:
    measuring an amount of a third microRNA, wherein the third microRNA is different from the first microRNA and the second microRNA, and the third microRNA is selected from the group consisting of: hsa-miR-15b, hsa-miR-181b, hsa-miR-191, hsa-miR-200c, and hsa-let-7g found in a sample, and
    comparing the amount of the third microRNA found in the sample to a standard amount of the third microRNA found in normal cells or to an amount of the third microRNA in a control sample,
    wherein the presence of an amplification in the amount of the third microRNA found in the sample relative to the standard or the control is further diagnostic for cancer; and
    wherein the absence of an amplification in the amount of the third microRNA found in the sample relative to the standard or the control is further diagnostic for the absence of cancer.

7. The method according to claim 6 further comprising:
    measuring an amount of a fourth microRNA, wherein the fourth microRNA is different from the first microRNA, the second microRNA and the third microRNA, and the fourth microRNA is selected from the group consisting of: hsa-miR-15b, hsa-miR-181b, hsa-miR-191, hsa-miR-200c, and hsa-let-7g found in a sample, and
    comparing the amount of the fourth microRNA found in the sample to a standard amount of the fourth microRNA found in normal cells or to an amount of the fourth microRNA in a control sample,
    wherein the presence of an amplification in the amount of the fourth microRNA found in the sample relative to the standard or the control is further diagnostic for cancer; and
    wherein the absence of an amplification in the amount of the fourth microRNA found in the sample relative to the standard or the control is further diagnostic for the absence of cancer.

8. The method according to claim 7, wherein the first microRNA is hsa-miR-15b, wherein the second microRNA is hsa-miR-181b, wherein the third microRNA is hsa-miR-191, and wherein the fourth microRNA is hsa-miR-200c, further comprising measuring a fifth microRNA, wherein the fifth microRNA is hsa-let-7g the measuring an amount of a fourth microRNA, wherein the fifth microRNA is hsa-let-7g, and
    comparing the amount of the fifth microRNA found in the sample to a standard amount of the fifth microRNA found in normal cells or to an amount of the fourth microRNA in a control sample,
    wherein the presence of an amplification in the amount of the fifth microRNA found in the sample relative to the standard or the control is further diagnostic for cancer; and
    wherein the absence of an amplification in the amount of the fifth microRNA found in the sample relative to the standard or the control is further diagnostic for the absence of cancer, is further prognostic for the high expected response to a cancer treatment.

9. A method of prognosticating an expected response to a cancer treatment or prognosticating an expected survival comprising the steps of:
    obtaining a biological sample from a subject in need of diagnosis or response or survival prognostication;
    measuring an amount of a first microRNA in the biological sample, wherein the first microRNA is hsa-miR-200c;
    comparing the amount of the first microRNA found in the biological sample to a standard amount of the first microRNA in normal or non-cancerous cells or to an amount of the first microRNA in a control sample,
    wherein the presence of an amplification in the amount of the first microRNA found in the sample relative to the standard or the control is prognostic for an expected low response to the cancer treatment or is prognostic for a low expected survival of the subject;
    wherein the absence of an amplification in the amount of the first microRNA found in the sample relative to the standard or control is prognostic for an expected high response to the cancer treatment, or is prognostic for an expected high survival, of the subject; and
    wherein the cancer is colorectal cancer.

10. A method of prognosticating an expected response to a cancer treatment comprising:
    measuring an amount of a first microRNA in the biological sample selected from the group consisting of hsa-let-7g and hsa-miR-181b;
    comparing the amount of the first microRNA found in the biological sample to a standard amount of the first microRNA found in normal or non-cancerous cells or to an amount of the first microRNA in a control sample,
    wherein the presence of an amplification in the amount of the first microRNA found in the sample relative to the standard or the control is prognostic for an expected high response to the cancer treatment;
    wherein the absence of an amplification in the amount of the first microRNA found in the sample relative to the standard or control is prognostic for an expected low response to the cancer treatment, wherein the cancer treatment is chemotherapy, and
wherein the cancer is colorectal cancer.

11. The method according to claim 10, wherein the first microRNA is hsa-miR-181b.

12. The method according to claim 10, wherein the first microRNA is hsa-let-7g.

13. The method according to claim 11, further comprising:
measuring an amount of a second microRNA in the biological sample, wherein the second microRNA is hsa-let-7g;
comparing the amount of the second microRNA found in the biological sample to a standard amount of the second microRNA found in normal or non-cancerous cells or to an amount of the second microRNA in a control sample,
wherein the presence of an amplification in the amount of the second microRNA found in the sample relative to the standard or the control is prognostic for an expected high response to the cancer treatment; and
wherein the absence of an amplification in the amount of the second microRNA found in the sample relative to the standard or control is prognostic for an expected low response to the cancer treatment.

* * * * *

UNITED STATES PATENT AND TRADEMARK OFFICE
CERTIFICATE OF CORRECTION

PATENT NO. : 8,343,719 B2
APPLICATION NO. : 12/513007
DATED : January 1, 2013
INVENTOR(S) : Ju et al.

Page 1 of 1

It is certified that error appears in the above-identified patent and that said Letters Patent is hereby corrected as shown below:

Title Page, Column 1, Item (56), OTHER PUBLICATIONS, Line 9, delete "nicroRNAs" and insert -- microRNAs --

In the Claims:

Column 16, Line 14, Claim 8, after "hsa-let-7g" delete "the"

Signed and Sealed this
Fourteenth Day of May, 2013

Teresa Stanek Rea
*Acting Director of the United States Patent and Trademark Office*